United States Patent
Beaty et al.

(10) Patent No.: US 8,540,935 B2
(45) Date of Patent: *Sep. 24, 2013

(54) SYSTEM AND METHOD FOR CODING INFORMATION ON A BIOSENSOR TEST STRIP

(75) Inventors: Terry A. Beaty, Indianapolis, IN (US); David W. Burke, Indianapolis, IN (US); Michael J. Celentano, Fishers, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/476,524

(22) Filed: May 21, 2012

(65) Prior Publication Data

US 2012/0228135 A1 Sep. 13, 2012

Related U.S. Application Data

(60) Continuation of application No. 13/094,901, filed on Apr. 27, 2011, now Pat. No. 8,182,764, which is a continuation of application No. 12/548,707, filed on Aug. 27, 2009, now Pat. No. 7,968,058, which is a division of application No. 11/097,606, filed on Apr. 1, 2005, now Pat. No. 7,601,299.

(51) Int. Cl.
*G01N 27/327* (2006.01)
*G01N 33/50* (2006.01)
*G01N 33/00* (2006.01)

(52) U.S. Cl.
USPC ... 422/50; 422/400; 204/403.02; 204/403.01; 204/400; 204/194; 204/193

(58) Field of Classification Search
USPC ............... 422/400, 50; 204/403.02, 403.01, 204/400, 194, 193
See application file for complete search history.

(56) References Cited

U.S. PATENT DOCUMENTS

| | | | |
|---|---|---|---|
| 7,601,299 B2 * | 10/2009 | Beaty et al. | 422/501 |
| 7,968,058 B2 * | 6/2011 | Beaty et al. | 422/403 |
| 8,182,764 B2 * | 5/2012 | Beaty et al. | 422/500 |
| 2005/0016845 A1 * | 1/2005 | Groll et al. | 204/403.1 |

* cited by examiner

*Primary Examiner* — Christine T Mui
(74) *Attorney, Agent, or Firm* — Woodard, Emhardt, Moriarty, McNett & Henry LLP

(57) ABSTRACT

The present invention provides a test strip for measuring a concentration of an analyte of interest in a biological fluid, wherein the test strip may be encoded with information that can be read by a test meter into which the test strip is inserted. In one embodiment, a first test strip comprises: a first measurement electrode connectable to a test meter; a first trace loop with a first associated resistance, where the first trace loop is connectable to the test meter; and a second trace loop with a second associated resistance, where the second trace loop is connectable to the test meter. The test meter is adapted to: receive the first test strip; connect to the first measurement electrode, the first trace loop, and the second trace loop; and obtain a first resistance ratio by comparing the first and second associated resistances.

15 Claims, 15 Drawing Sheets

SYSTEM AND METHOD FOR CODING INFORMATION ON A BIOSENSOR TEST STRIP

REFERENCE TO RELATED APPLICATIONS

This application is a continuation of U.S. patent application Ser. No. 13/094,901 filed Apr. 27, 2011 now U.S. Pat. No. 8,182,764, which is a continuation of U.S. patent application Ser. No. 12/548,707 filed Aug. 27, 2009 now U.S. Pat. No. 7,968,058, which is a divisional application of U.S. patent application Ser. No. 11/097,606, filed Apr. 1, 2005 now U.S. Pat. No. 7,601,299.

TECHNICAL FIELD OF THE INVENTION

The present invention relates to an apparatus for use in measuring concentrations of an analyte in a biological fluid. The invention relates more particularly to a system and method for coding information on a biosensor test strip.

BACKGROUND OF THE INVENTION

Measuring the concentration of substances in biological fluids is an important tool for the diagnosis and treatment of many medical conditions. For example, the measurement of glucose in body fluids, such as blood, is crucial to the effective treatment of diabetes.

Diabetic therapy typically involves two types of insulin treatment: basal, and meal-time. Basal insulin refers to continuous, e.g. time-released insulin, often taken before bed. Meal-time insulin treatment provides additional doses of faster acting insulin to regulate fluctuations in blood glucose caused by a variety of factors, including the metabolization of sugars and carbohydrates. Proper regulation of blood glucose fluctuations requires accurate measurement of the concentration of glucose in the blood. Failure to do so can produce extreme complications, including blindness and loss of circulation in the extremities, which can ultimately deprive the diabetic of use of his or her fingers, hands, feet, etc.

Multiple methods are known for determining the concentration of analytes in a blood sample, such as, for example, glucose. Such methods typically fall into one of two categories: optical methods and electrochemical methods. Optical methods generally involve spectroscopy to observe the spectrum shift in the fluid caused by concentration of the analyte, typically in conjunction with a reagent that produces a known color when combined with the analyte. Electrochemical methods generally rely upon the correlation between a current (Amperometry), a potential (Potentiometry) or accumulated charge (Coulometry) and the concentration of the analyte, typically in conjunction with a reagent that produces charge-carriers when combined with the analyte. See, for example, U.S. Pat. Nos. 4,233,029 to Columbus, 4,225,410 to Pace, 4,323,536 to Columbus, 4,008,448 to Muggli, 4,654,197 to Lilja et al., 5,108,564 to Szuminsky et al., 5,120,420 to Nankai et al., 5,128,015 to Szuminsky et al., 5,243,516 to White, 5,437,999 to Diebold et al., 5,288,636 to Pollmann et al., 5,628,890 to Carter et al., 5,682,884 to Hill et al., 5,727,548 to Hill et al., 5,997,817 to Crismore et al., 6,004,441 to Fujiwara et al., 4,919,770 to Priedel, et al., and 6,054,039 to Shieh, which are hereby incorporated herein by reference in their entireties. The biosensor for conducting the tests is typically a disposable test strip having a reagent thereon that chemically reacts with the analyte of interest in the biological fluid. The test strip is mated to a nondisposable test meter such that the test meter can measure the reaction between the analyte and the reagent in order to determine and display the concentration of the analyte to the user.

It is common practice in such test meter/test strip systems to ensure proper identification of the test strip in order to ensure proper test results. For example, a single test meter may be able to analyze several different types of test strips, wherein each type of test strip is designed to test for the presence of a different analyte in the biological fluid. In order to properly conduct the test, the test meter must know which type of test is to be performed for the test strip currently in use.

Also, lot-to-lot variations in the test strips normally require calibration information to be loaded into the test meter in order to ensure accurate test results. A common practice for downloading such calibration information into the test meter is the use of an electronic read-only memory key (ROM key) that is inserted into a socket of the test meter. Because this calibration data may only be accurate for a particular production lot of test strips, the user is usually asked to confirm that the lot number of the test strip currently in use matches the lot number for which the ROM key was programmed.

Many other instances in which it is desirable to have information relating to the test strip are known to those having skill in the art. Prior art attempts to code information onto the test strip for reading by the test meter have suffered from many problems, including a severely limited amount of information that can be coded and the use of relatively large amounts of test strip surface area for the information coding function.

Thus, a system and method are needed that will allow information to be coded onto a biosensor for reading of the information by the test meter. The present invention is directed toward meeting this need.

SUMMARY OF THE INVENTION

The present invention provides a test strip for measuring a concentration of an analyte of interest in a biological fluid, wherein the test strip may be encoded with information that can be read by a test meter into which the test strip is inserted. In one form of the invention, a system for measuring a concentration of an analyte of interest in a biological fluid is disclosed. The system comprises a test meter and a first test strip with a first mask configuration, a first resistive element, and a second resistive element. The first mask configuration comprises: a first measurement electrode that is connectable to the test meter; a first trace loop with a first associated resistance and a first gap, where the first trace loop is connectable to the test meter; and a second trace loop with a second associated resistance and a second gap, where the second trace loop is connectable to the test meter. The first resistive element is conductively connected to the first trace loop and bridges the first gap, and the second resistive element is conductively connected to the second trace loop and bridges the second gap. The system further comprises a second test strip with a second mask configuration, a third resistive element, and a fourth resistive element, where the second mask configuration is substantially similar to the first mask configuration. The second mask configuration comprises: a second measurement electrode connectable to the test meter; a third trace loop with a third associated resistance and a third gap, where the trace loop is connectable to the test meter; and a fourth trace loop with a fourth associated resistance and a fourth gap, where the fourth trace loop is connectable to the test meter. The third resistive element is conductively connected to the third trace loop and bridges the third gap, and the fourth resistive element is conductively connected to the fourth trace loop and bridges the fourth gap. The test meter is adapted to receive the first and second test strips, connect to the first and second measurement electrodes, and connect to the first and second trace loops. The test meter is further adapted to obtain a first resistance ratio by comparing the first and second associated resistances, connect to the third and fourth trace loops, and obtain a second resistance ratio by comparing the third and fourth associated resistances. The test meter may be further adapted to correlate each of the first and second resistance ratios to one or more predetermined values that correspond to information about the first and/or second strips.

In another form of the invention, a system for measuring a concentration of an analyte of interest in a biological fluid is disclosed. The system comprises a test meter and a first test strip. The first test strip comprises: a first measurement electrode connectable to the test meter; a first trace loop with a first associated resistance, where the first trace loop is connectable to the test meter; and a second trace loop with a second associated resistance, where the second trace loop is connectable to the test meter. The test meter is adapted to: receive the first test strip; connect to the first measurement electrode, the first trace loop, and the second trace loop; and obtain a first resistance ratio by comparing the first and second associated resistances.

In another form of the invention, a method for measuring a concentration of an analyte of interest in a biological fluid is disclosed. The method comprises providing a test meter and providing a first test strip. The first test strip comprises: a first measurement electrode connectable to the test meter; a first trace loop with a first associated resistance, where the first trace loop is connectable to the test meter; and a second trace loop with a second associated resistance, where the second trace loop is connectable to the test meter. The method further comprises: receiving the first test strip into the test meter; communicatively connecting the first measurement electrode, the first trace loop, and the second trace loop with the test meter; and obtaining a first resistance ratio by comparing the first and second associated resistances.

In another form of the invention, a method for encoding information readable by a test meter onto a test strip, where the test strip adapted for measuring a concentration of an analyte of interest in a biological fluid, is disclosed. The method comprises selecting a first resistance ratio associated with a first word desired to be encoded on the test strip and forming a measurement electrode on the surface of the test strip substrate, where the measurement electrode is connectable to a test meter. The method further comprises forming a first electrical trace and a second electrical trace on the surface of the test strip substrate, where the resistance of each of the first and second electrical traces are obtainable by the test meter, and where the ratio of the resistance of the first electrical trace and the resistance of the second electrical trace effectively matches the first resistance ratio.

BRIEF DESCRIPTION OF THE DRAWINGS

The invention will be further described, by way of example only, with reference to the accompanying drawings, in which.

DETAILED DESCRIPTION OF THE ILLUSTRATED EMBODIMENTS

Figure 1:
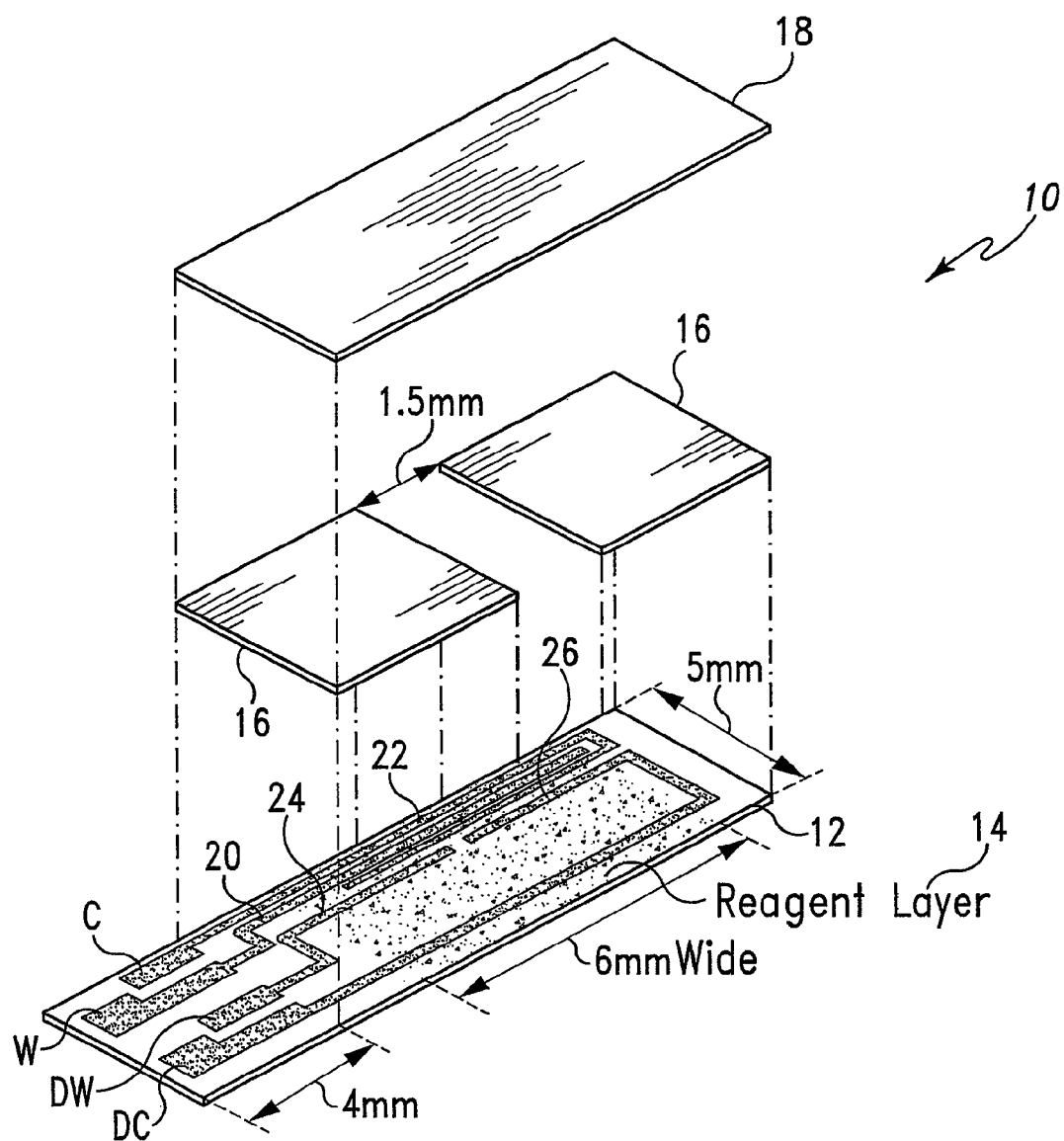
FIG. 1 is an exploded perspective view of a first typical test strip for use in measuring the concentration of an analyte of interest in a biological fluid.

For the purposes of promoting an understanding of the principles of the invention, reference will now be made to the embodiment illustrated in the drawings, and specific language will be used to describe that embodiment. It will nevertheless be understood that no limitation of the scope of the invention is intended. Alterations and modifications in the illustrated device, and further applications of the principles of the invention as illustrated therein, as would normally occur to one skilled in the art to which the invention relates are contemplated, are desired to be protected. In particular, although the invention is discussed in terms of a blood glucose meter, it is contemplated that the invention can be used with devices for measuring other analytes and other sample types. Such alternative embodiments require certain adaptations to the embodiments discussed herein that would be obvious to those skilled in the art.

Although the system and method of the present invention may be used with test strips having a wide variety of designs and made with a wide variety of construction techniques and processes, a typical electrochemical test strip is illustrated in FIG. 1, and indicated generally at 10. Referring to FIG. 1, the test strip 10 comprises a bottom substrate 12 formed from an opaque piece of 350 μm thick polyester (such as Melinex 329 available from DuPont) coated on its top surface with a 50 nm conductive (gold) layer (by sputtering or vapor deposition, for example). Electrodes, connecting traces and contact pads therefore are then patterned in the conductive layer by a laser ablation process. The laser ablation process is performed by means of an excimer laser which passes through a chromeon-quartz mask. The mask pattern causes parts of the laser field to be reflected while allowing other parts of the field to pass through, creating a pattern on the gold which is ablated where contacted by the laser light. The laser ablation process is described in greater detail hereinbelow. For example, working 20, counter 22, dose sufficiency working 24, and dose sufficiency counter 26 electrodes may be formed as shown and coupled, respectively, to measurement contact pads W, C, DW and DC. These contact pads provide a conductive area upon the test strip 10 to be contacted by a connector contact of the test meter once the test strip 10 is inserted into the test meter. As used herein, the phrase "measurement contact pad" is defined as a contact pad on the test strip that is conductively coupled to a measurement electrode of the test strip and is a primary contact pad for measuring a characteristic of a body fluid sample, such as sample size or the concentration of an analyte in the sample. As used herein, the phrase "information contact pad" is defined as a contact pad on the test strip that is not a measurement contact pad and is used for encoding information onto the test strip.

The bottom substrate 12 is then coated in the area extending over the electrodes with a reagent layer 14 as a continuous, extremely thin reagent film. The reagent layer 14 is a stripe of approximately 6 millimeters width across the substrate 12 in the region labeled "Reagent Layer" on FIG. 1. For example, this region may be coated at a wet-coat weight of 50 grams per square meter of coated surface area. The reagent strip is dried conventionally with an in-line drying system where the nominal air temperature is at 110° C. The rate of processing is nominally 30-38 meters per minute and depends upon the rheology of the reagent.

The materials are processed in continuous reels such that the electrode pattern is orthogonal to the length of the reel, in the case of the substrate 12. Once the substrate 12 has been coated with reagent, the spacers 16 are slit and placed in a reel-to-reel process onto the substrate 12. Two spacers 16 formed from 100 μm polyester (for example, Melinex 329 available from DuPont) coated with 25 μm PSA (hydrophobic adhesive) on both the dorsal and ventral surfaces are applied to the bottom substrate 12, such that the spacers 16 are separated by 1.5 mm and the working, counter and dose sufficiency electrodes are centered in this gap. A top foil layer 18 formed from 100 μm polyester coated with a hydrophilic film on its ventral surface (using the process described in U.S. Pat. No. 5,997,817) is placed over the spacers 16. The hydrophilic film is coated with a mixture of Vitel and Rhodapex surfactant at a nominal thickness of 10 microns. The top foil layer 18 is laminated using a reel-to-reel process. The test strips can then be produced from the resulting reels of material by means of slitting and cutting.

Although the basic test strip 10 illustrated in FIG. 1 can provide accurate measurements of blood glucose in a whole blood sample, it does not provide any means for the test meter into which it is inserted to identify anything about the test strip. The present invention presents systems by which information relating to the test strip can be coded directly onto the test strip itself, such that this information can be conveyed to a test meter into which the test strip is inserted.

One method of preparing a test strip encoded with information as described herein is by the use of laser ablation techniques. Examples of the use of these techniques in preparing electrodes for biosensors are described in United States Patent Application Publication Number 2002/0192115, entitled "Biosensor," filed May 25, 2001, and in U.S. Pat. No. 6,662,439, entitled "Laser Defined Features for Patterned Laminates and Electrodes," issued Dec. 16, 2003, both disclosures hereby incorporated herein by reference in their entireties. As used herein, the term "encode" is defined as to convert from one system of communication into another and includes situations where particular aspects of a test strip are controlled or manipulated in a manner that will provide information to a test meter. The systems and methods disclosed herein include analog comparative methods and situations where information is read by a test meter, conveyed to the test meter, and gleaned from the test strip.

It is desirable in the present invention to provide for the accurate placement of the electrical components relative to one another and to the overall biosensor. In another embodiment, the relative placement of components is achieved, at least in part, by the use of broad field laser ablation that is performed through a mask or other device that has a precise pattern for the electrical components. This allows accurate positioning of adjacent edges, which is further enhanced by the close tolerances for the smoothness of the edges.

Figure 2:
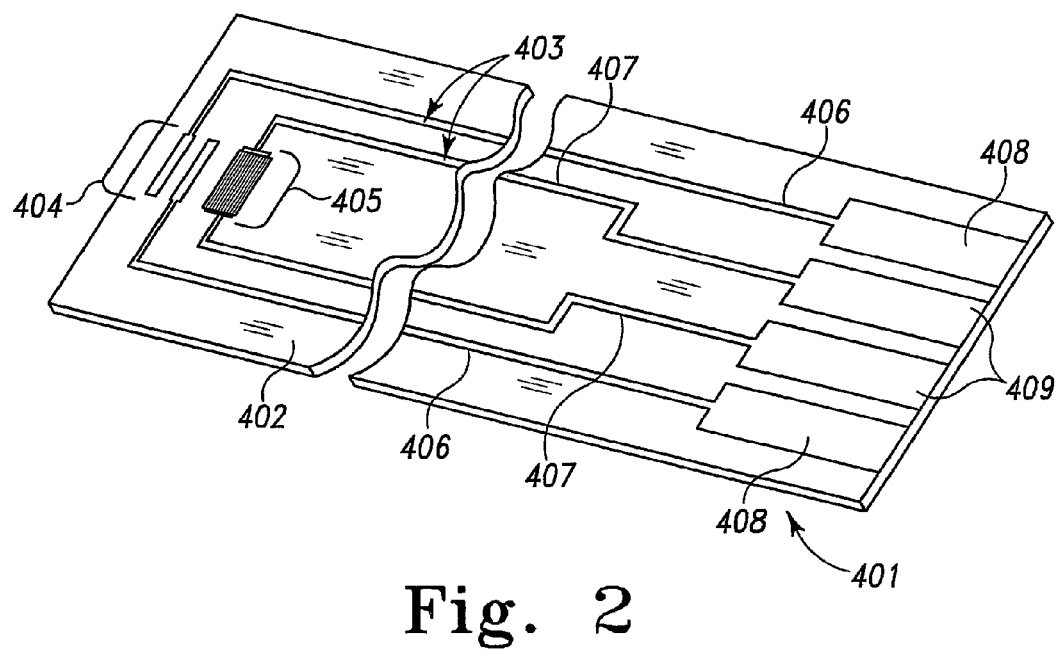
FIG. 2 is a perspective view of a second typical test strip for use in measuring the concentration of an analyte of interest in a biological fluid.

FIG. 2 illustrates a simple biosensor 401 useful for illustrating the laser ablation process of the present invention, including a substrate 402 having formed thereon conductive material 403 defining electrode systems comprising a first electrode set 404 and a second electrode set 405, and corresponding traces 406, 407 and contact pads 408, 409, respectively. The conductive material 403 may contain pure metals or alloys, or other materials, which are metallic conductors. The conductive material is generally absorptive at the wavelength of the laser used to form the electrodes and of a thickness amenable to rapid and precise processing. Non-limiting examples include aluminum, carbon, copper, chromium, gold, indium tin oxide (ITO), palladium, platinum, silver, tin oxide/gold, titanium, mixtures thereof, and alloys or metallic compounds of these elements. In some embodiments, the conductive material includes noble metals or alloys or their oxides. In other embodiments, the conductive material includes gold, palladium, aluminum, titanium, platinum, ITO and chromium. In still other embodiments, the conductive material ranges in thickness from about 10 nm to 80 nm. In further embodiments, the conductive material ranges in thickness from about 30 nm to 70 nm. In still further embodiments, the conductive material thickness equals approximately 50 nm. It is appreciated that the thickness of the conductive material depends upon the transmissive property of the material and other factors relating to use of the biosensor.

While not illustrated, it is appreciated that the resulting patterned conductive material can be coated or plated with additional metal layers. For example, the conductive material may be copper, which is then ablated with a laser into an electrode pattern; subsequently, the copper may be plated with a titanium/tungsten layer, and then a gold layer, to form the desired electrodes. In some embodiments, a single layer of conductive material is used, which lies on the base 402. Although not generally necessary, it is possible to enhance adhesion of the conductive material to the base, as is well known in the art, by using seed or ancillary layers such as chromium nickel or titanium. In other embodiments, biosensor 401 has a single layer of gold, palladium, platinum or ITO.

Figure 3:
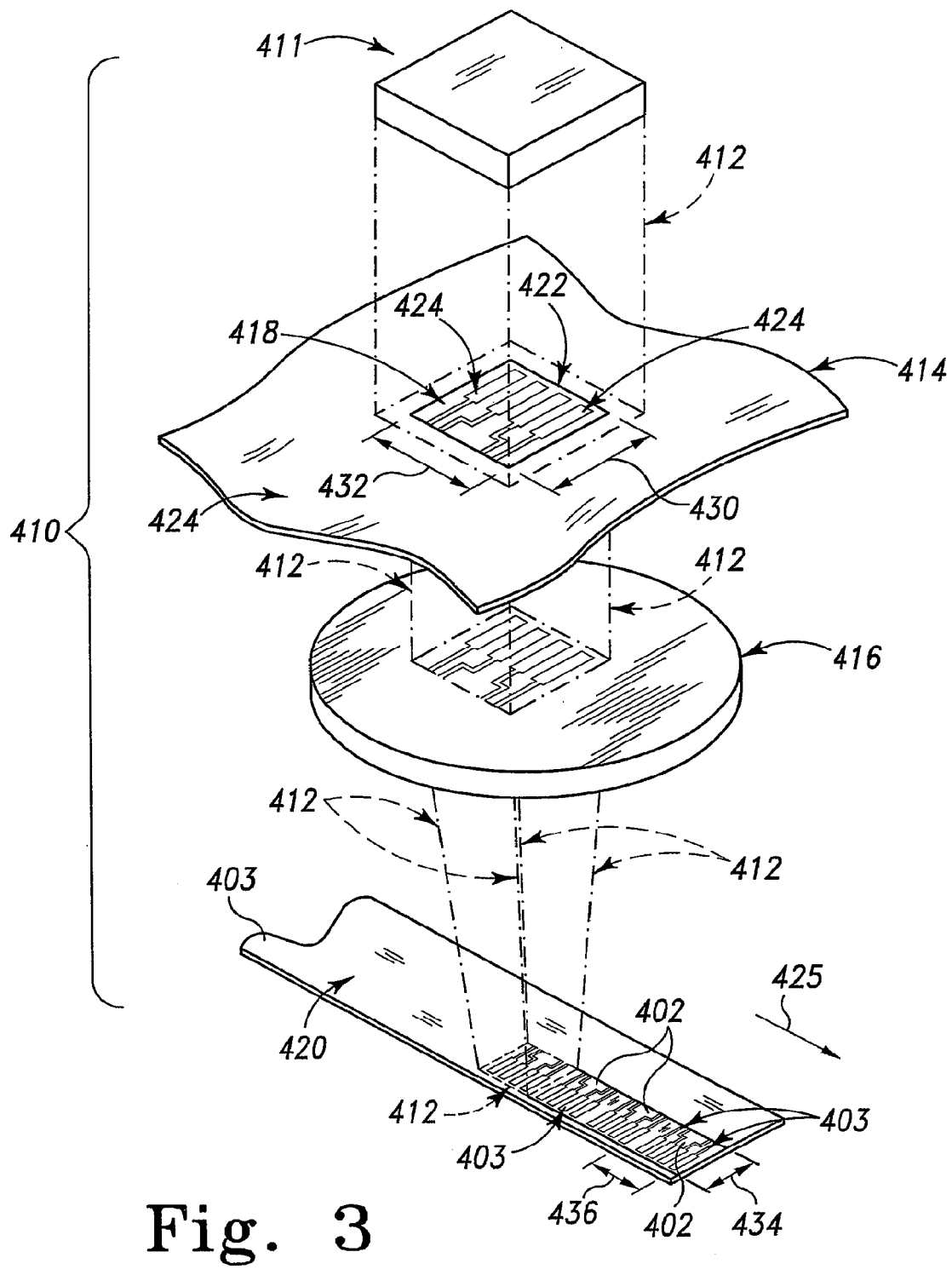
FIG. 3 illustrates a view of an ablation apparatus suitable for use with the present invention.
Figure 4:
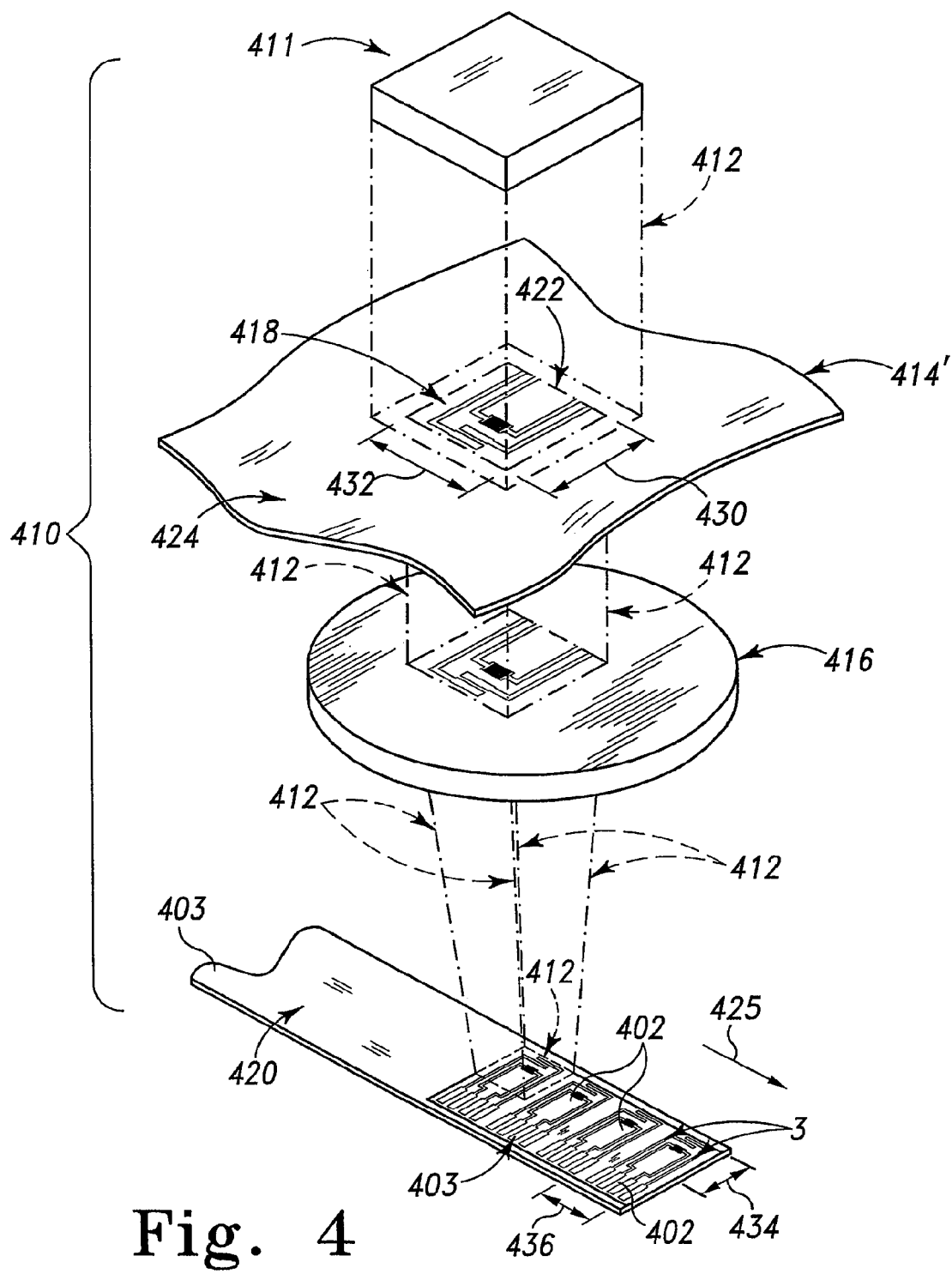
FIG. 4 is a view of the laser ablation apparatus of FIG. 3 showing a second mask.
Figure 5:
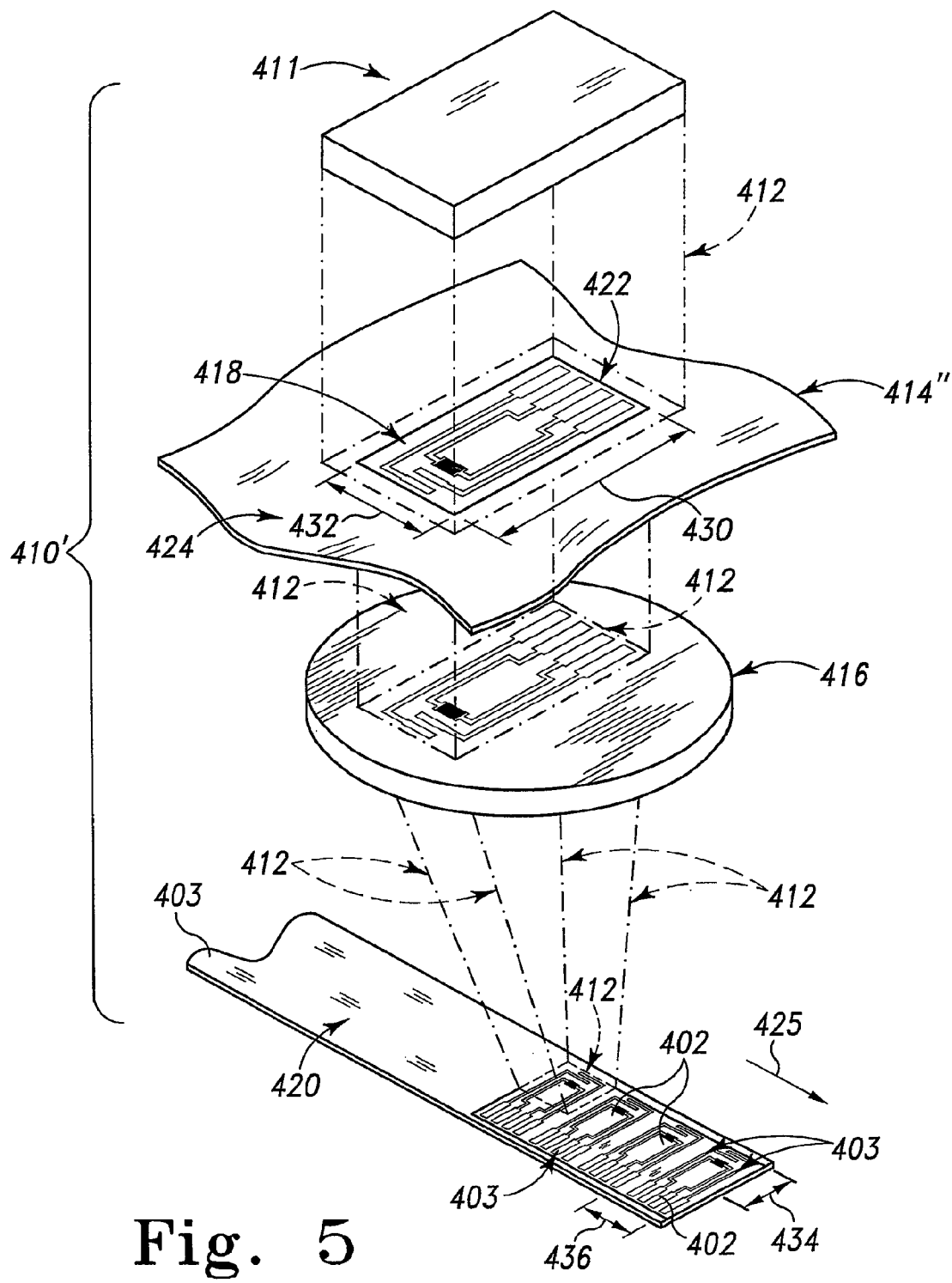
FIG. 5 is a view of an ablation apparatus suitable for use with the present invention.

Biosensor 401 is illustratively manufactured using two apparatuses 410, 410', shown in FIGS. 3-5, respectively. It is appreciated that unless otherwise described, the apparatuses 410, 410' operate in a similar manner. Referring first to FIG. 3, biosensor 401 is manufactured by feeding a roll of ribbon 420 having an 80 nm gold laminate, which is about 40 mm in width, into a custom fit broad field laser ablation apparatus 410. The apparatus 410 comprises a laser source 411 producing a beam of laser light 412, a chromium-plated quartz mask 414, and optics 416. It is appreciated that while the illustrated optics 416 is a single lens, in some embodiments optics 416 is a variety of lenses that cooperate to make the light 412 in a pre-determined shape.

A non-limiting example of a suitable ablation apparatus 410 (FIGS. 3-4) is a customized MicrolineLaser 200-4 laser system commercially available from LPKF Laser Electronic GmbH, of Garbsen, Germany, which incorporates an LPX-400, LPX-300 or LPX-200 laser system commercially available from Lambda Physik AG, Göttingen, Germany and a chromium-plated quartz mask commercially available from International Phototool Company, Colorado Springs, Co.

For the MicrolineLaser 200-4 laser system (FIGS. 3-4), the laser source 411 is a LPX-200 KrF-UV-laser. It is appreciated, however, that higher wavelength UV lasers can be used in accordance with this disclosure. The laser source 411 works at 248 nm, with a pulse energy of 600 mJ, and a pulse repeat frequency of 50 Hz. The intensity of the laser beam 412 can be infinitely adjusted between 3% and 92% by a dielectric beam attenuator (not shown). The beam profile is 27×15 mm² (0.62 sq. inch) and the pulse duration 25 ns. The layout on the mask 414 is homogeneously projected by an optical elements beam expander, homogenizer, and field lens (not shown). The performance of the homogenizer has been determined by measuring the energy profile. The imaging optics 416 transfer the structures of the mask 414 onto the ribbon 420. The imaging ratio is 2:1 to allow a large area to be removed on the one hand, but to keep the energy density below the ablation point of the applied chromium mask on the other hand. While an imaging of 2:1 is illustrated, it is appreciated that the any number of alternative ratios are possible in accordance with this disclosure depending upon the desired design requirements. The ribbon 420 moves as shown by arrow 425 to allow a number of layout segments to be ablated in succession.

The positioning of the mask 414, movement of the ribbon 420, and laser energy are computer controlled. As shown in FIG. 3, the laser beam 412 is projected onto the ribbon 420 to be ablated. Light 412 passing through the clear areas or windows 418 of the mask 414 ablates the metal from the ribbon 420. Chromium coated areas 424 of the mask 414 blocks the laser light 412 and prevent ablation in those areas, resulting in a metallized structure on the ribbon 420 surface. Referring now to FIG. 4, a complete structure of electrical components may require additional ablation steps through a second mask 414'. It is appreciated that depending upon the optics and the size of the electrical component to be ablated, that only a single ablation step or greater than two ablation steps may be necessary in accordance with this disclosure. Further, it is appreciated that instead of multiple masks, that multiple fields may be formed on the same mask in accordance with this disclosure.

Specifically, a second non-limiting example of a suitable ablation apparatus 410' (FIG. 5) is a customized laser system commercially available from LPKF Laser Electronic GmbH, of Garbsen, Germany, which incorporates a Lambda STEEL (Stable energy eximer laser) laser system commercially available from Lambda Physik AG, Göttingen, Germany and a chromium-plated quartz mask commercially available from International Phototool Company, Colorado Springs, Co. The laser system features up to 1000 mJ pulse energy at a wavelength of 308 nm. Further, the laser system has a frequency of 100 Hz. The apparatus 410' may be formed to produce biosensors with two passes as shown in FIGS. 3 and 4. In certain embodiments, the optics of apparatus 410' permit the formation of a 10×40 mm pattern in a 25 ns single pass.

While not wishing to be bound to a specific theory, it is believed that the laser pulse or beam 412 that passes through the mask 414, 414', 414" is absorbed within less than 1 µm of the surface 402 on the ribbon 420. The photons of the beam 412 have an energy sufficient to cause photo-dissociation and the rapid breaking of chemical bonds at the metal/polymer interface. It is believed that this rapid chemical bond breaking causes a sudden pressure increase within the absorption region and forces material (metal film 403) to be ejected from the polymer base surface. Since typical pulse durations are around 20-25 nanoseconds, the interaction with the material occurs very rapidly and thermal damage to edges of the conductive material 403 and surrounding structures is minimized. The resulting edges of the electrical components have high edge quality and accurate placement as contemplated by the present invention.

Fluence energies used to remove or ablate metals from the ribbon 420 are dependent upon the material from which the ribbon 420 is formed, adhesion of the metal film to the base material, the thickness of the metal film, and possibly the process used to place the film on the base material, i.e. supporting and vapor deposition. Fluence levels for gold on KALADEX® range from about 50 to about 90 mJ/cm², on polyimide about 100 to about 120 mJ/cm², and on MELINEX® about 60 to about 120 mJ/cm². It is understood that fluence levels less than or greater than the above mentioned can be appropriate for other base materials in accordance with the disclosure.

Patterning of areas of the ribbon 420 is achieved by using the masks 414, 414' and 414". Each mask 414, 414' and 414" illustratively includes a mask field 422 containing a precise two-dimensional illustration of a pre-determined portion of the electrode component patterns to be formed. FIG. 3 illustrates the mask field 422 including contact pads and a portion of traces. As shown in FIG. 4, the second mask 414' contains a second corresponding portion of the traces and the electrode patterns containing fingers. As previously described, it is appreciated that depending upon the size of the area to be ablated, the mask 414 can contain a complete illustration of the electrode patterns (FIG. 5), or portions of patterns different from those illustrated in FIGS. 3 and 4 in accordance with this disclosure. It is contemplated that in one aspect of the present invention, the entire pattern of the electrical components on the test strip are laser ablated at one time, i.e., the broad field encompasses the entire size of the test strip, as illustrated by mask 414" in FIG. 5. In the alternative, and as illustrated in FIGS. 3 and 4, portions of the entire biosensor are done successively.

While mask 414 will be discussed hereafter, it is appreciated that unless indicated otherwise, the discussion will apply to masks 414', 414" as well. Referring to FIG. 3, areas 424 of the mask field 422 protected by the chrome will block the projection of the laser beam 412 to the ribbon 420. Clear areas or windows 418 in the mask field 422 allow the laser beam 412 to pass through the mask 414 and to impact predetermined areas of the ribbon 420. As shown in FIG. 3, the clear area 418 of the mask field 422 corresponds to the areas of the ribbon 420 from which the conductive material 403 is to be removed.

Further, the mask field 422 has a length shown by line 430 and a width as shown by line 432. Given the imaging ratio of 2:1 of the LPX-200, it is appreciated that the length 430 of the mask is two times the length of a length 434 of the resulting pattern and the width 432 of the mask is two times the width of a width 436 of the resulting pattern on ribbon 420. The optics 416 reduces the size of laser beam 412 that strikes the ribbon 420. It is appreciated that the relative dimensions of the mask field 422 and the resulting pattern can vary in accordance with this disclosure. Mask 414' (FIG. 4) is used to complete the two-dimensional illustration of the electrical components.

Continuing to refer to FIG. 3, in the laser ablation apparatus 410 the excimer laser source 411 emits beam 412, which passes through the chrome-on-quartz mask 414. The mask field 422 causes parts of the laser beam 412 to be reflected while allowing other parts of the beam to pass through, creating a pattern on the gold film where impacted by the laser beam 412. It is appreciated that ribbon 420 can be stationary relative to apparatus 410 or move continuously on a roll through apparatus 410. Accordingly, non-limiting rates of movement of the ribbon 420 can be from about 0 m/min to about 100 m/min. In some embodiments, other non-limiting rates of movement of the ribbon 420 can be from about 30 m/min to about 60 m/min. It is appreciated that the rate of movement of the ribbon 420 is limited only by the apparatus 410 selected and may well exceed 100 m/min depending upon the pulse duration of the laser source 411 in accordance with the present disclosure.

Once the pattern of the mask 414 is created on the ribbon 420, the ribbon is rewound and fed through the apparatus 410 again, with mask 414' (FIG. 4). It is appreciated, that alternatively, laser apparatus 410 could be positioned in series in accordance with this disclosure. Thus, by using masks 414, 414', large areas of the ribbon 420 can be patterned using step-and-repeat processes involving multiple mask fields 422 in the same mask area to enable the economical creation of intricate electrode patterns and other electrical components on a substrate of the base, the precise edges of the electrode components, and the removal of greater amounts of the metallic film from the base material.

The ability to code information directly onto the test strip can dramatically increase the capabilities of the test strip and enhance its interaction with the test meter. For example, it is well known in the art to supply the test meter with calibration data applicable to any given manufacturing lot of test strips. Typically, this is done by supplying a read-only memory key (ROM key) with each vial of test strips, where the ROM key has encoded thereon the calibration data applicable to the test strips in the vial. Before using the test strips from the vial, the user inserts the ROM key into a port in the test meter so that the test meter may have access to this data while performing tests using the test strip. The quality of the measurement result can be verified by allowing the meter to electronically assess the applicability of the ROM key data to the test strip currently inserted into the meter, without the need for an optical reader to read bar code information on the test strip as has been taught in the prior art.

Figure 6:
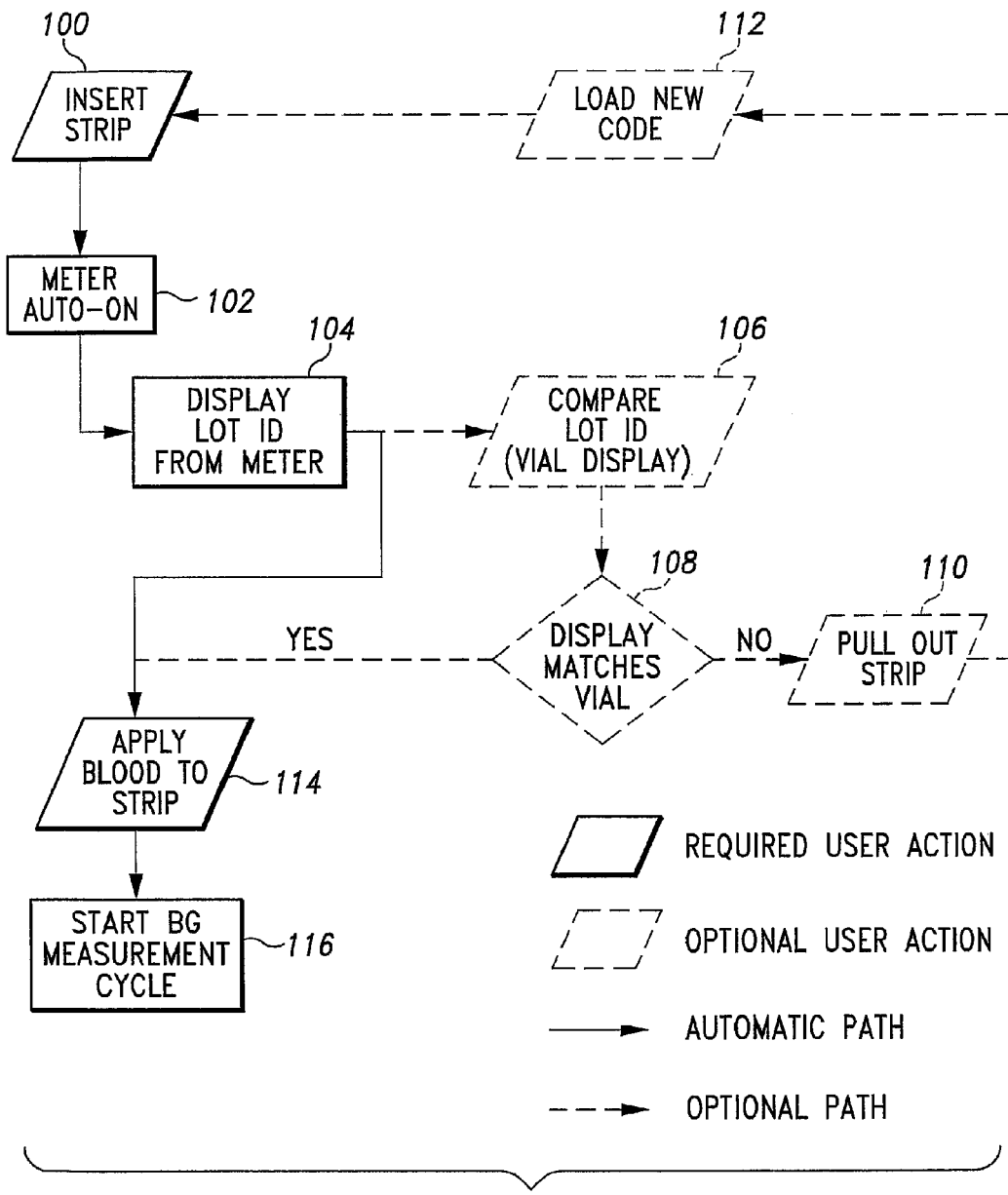
FIG. 6 is a schematic process flow diagram of a prior art process for verifying the applicability of the calibration data in the test meter to the test strip currently inserted into the test meter.

Current commercially-available products require the user to be involved in verifying the correct ROM key has been inserted into the test meter for the test strip currently being used. For example, FIG. 6 illustrates a typical prior art process for verifying the match between the ROM key data and the test strip lot identification (ID) number. Prior to executing this process, the ROM key has been inserted into the test meter, the ROM data has been loaded into the test meter, and the test meter is turned off. The process begins by inserting a test strip (step 100) into the test meter, which causes the test meter to automatically turn on (step 102). The test meter displays the lot ID of the currently loaded calibration data (step 104) in order to give the user the chance to verify that this lot ID matches the lot ID printed on the vial/package (for example) containing a plurality of test strips from the same production lot as the test strip currently inserted into the test meter.

Because the process relies upon the user to perform this check, there is no way to guarantee that it is done or if it is, that it is done accurately. The process of FIG. 6 therefore indicates an optional step for the user to compare the lot ID on the test meter display to the lot ID on the test strip vial (step 106) and to determine (step 108) if there is a match. If the two lot IDs do not match, then the user should remove the test strip (step 110) and insert the ROM key that matches the test strip vial into the test meter (step 112) so that the proper calibration code can be loaded into the test meter. The process would then start over at step 100 with the insertion of the test strip. Once it has been determined that the test meter's calibration code lot ID matches the lot ID of the test strip (step 108), then the measurement sequence can continue by applying blood to the test strip (step 24) and beginning the blood glucose measurement cycle (step 116).

It will be appreciated that responsibility for verification of the accuracy of the measurement calibration data has been placed completely in the hands of the user in the prior art process of FIG. 6. It is sometimes encountered that users ignore stated use instructions provided with the test strips. One such example is the removal of test strips from a first vial that were manufactured in lot X and consolidating these test strips into a second vial containing test strips manufactured in lot Y. Therefore, it is desirable to bring lot specific calibration information to the individual test strip level instead of to the vial level as is done in the prior art.

Figure 7:
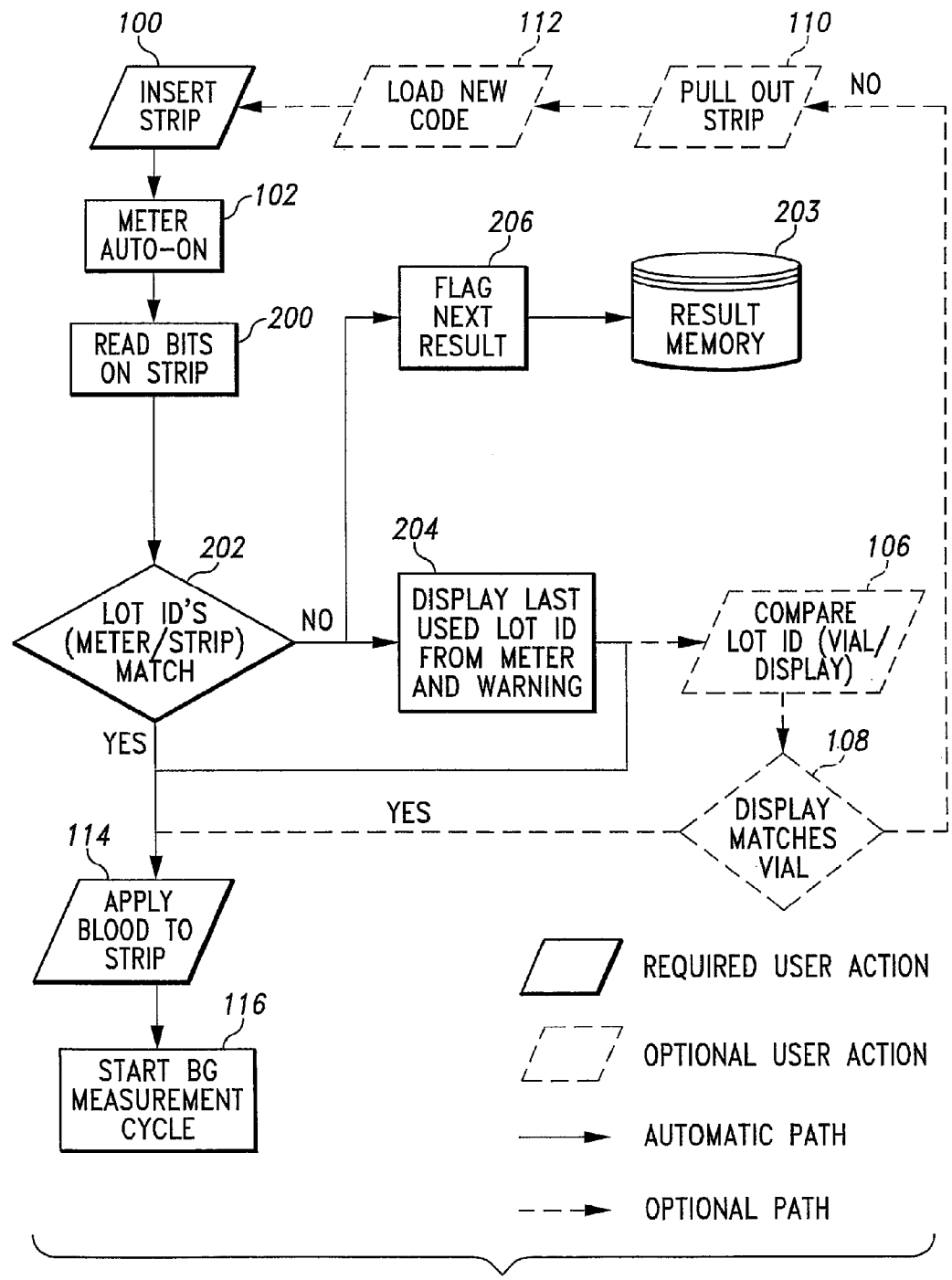
FIG. 7 is a schematic process flow diagram of a first embodiment process of the present invention for verifying the applicability of the calibration data in the test meter to the test strip currently inserted into the test meter.

In order to remove the possibility of human error or neglect from the process, and to thereby improve the quality of the measurement, the information contact pads of the present invention allow the test meter itself to perform checks as to the applicability of the currently loaded calibration data to the currently inserted test strip. A first embodiment process of the present invention to allow the test meter to actively participate in such verification is illustrated in FIG. 7. The steps of the process of FIG. 7 that are identical to the corresponding steps in FIG. 6 are numbered with the same reference designators.

Prior to executing this process, the ROM key has been inserted into the test meter, the ROM data has been loaded into the test meter, and the test meter is turned off. The process begins by inserting a test strip (step 100) into the test meter, which causes the test meter to automatically turn on (step 102). The test meter then measures the conductivity between the various information and measurement contact pads on the test strip that have been designated for encoding information onto the test strip in order to ascertain the lot or family ID of the test strip (step 200). Depending upon the quantity of information that may be encoded onto the test strip, it may or may not be possible to code a unique production lot number onto the test strip. If there is not sufficient space for unique production lot IDs to be encoded, it is still possible to encode calibration family information onto the test strip. For example, the test strips usable in the test meter may be of two or more families where significant differences exist between the family test strip designs. For example, two families may use a different reagent on the test strip. In such situations, the test meter can still verify that the loaded calibration data matches the test strip family encoded onto the test strip, even if it is not possible to verify the precise production lot of the test strip. Therefore, as used herein, the phrase "lot ID" is intended to encompass any information that identifies a group to which the test strip or calibration data belongs, even if that group is not as small as a production lot of the test strip.

Returning to the process of FIG. 7, the test meter compares (step 202) the lot ID of the calibration data stored within the ROM key currently inserted into the meter (or calibration data previously-loaded into the test meter internal memory) to the lot ID read from the test strip. If they do not match, the test meter displays the lot ID of the currently loaded calibration data (step 204) and a warning in order to give the user the chance to insert a correct test strip or to insert a different ROM key into the test meter. Alternatively, the test meter may simply display an error message to the user. The fact that the lot IDs do not match is flagged (step 206) in the test meter's result memory 208 so that there is a record in the memory 208 that the measurement result obtained is suspect in view of the discrepancy in the lot IDs. Alternatively, the user may be prohibited from running a test and the process may be aborted.

Because in some embodiments it is desired that the test meter not be completely disabled if the lot IDs do not match, the process of FIG. 7 indicates an optional step for the user to compare the lot ID on the test meter display to the lot ID on the test strip vial (step 106) and to determine (step 108) if there is a match. If the two lot IDs do not match, then the user should remove the test strip (step 110) and insert the ROM key that matches the test strip vial into the test meter (step 112) so that the proper calibration code can be loaded into the test meter. The process would then start over at step 100 with the insertion of the test strip.

Also optionally, if the test meter has the capacity to store more than one calibration dataset within the meter's internal memory, then the meter may determine the multiple lot IDs of calibration data that may be stored within the test meter and automatically choose the calibration dataset that matches the test strip currently inserted into the meter. The meter can then return to step 24.

Once it has been determined that the test meter's calibration code lot ID matches the lot ID of the test strip (step 108), then the measurement sequence can continue by applying blood to the test strip (step 24) and beginning the blood glucose measurement cycle (step 116). It will be appreciated that the process of FIG. 7 represents an improvement over the prior art process of FIG. 6 in that the user is automatically warned when the lot ID of the test strip does not match the lot ID of the currently-selected calibration dataset. Furthermore, if a test is conducted with this mismatched combination, then the result memory within the test meter is flagged to indicate that the result may not be as accurate as would be the case if the correct calibration dataset were used.

As a further example of the usefulness of encoding information directly onto the test strip, the present invention allows the test strip to activate or deactivate certain features programmed into the test meter. For example, a single test meter may be designed to be used in several different geographic markets, where a different language is spoken in each market. By encoding the test strips with information indicating in which market the test strips were sold, the encoded information can cause the test meter to display user instructions and data in a language that is appropriate for that market. Also, a meter may be designed for sale in a certain geographic market and it is desired that the meter not be used with test strips obtained in a different geographic market (for example when governmental regulations require the test strips sold in one geographic market to have different features than those sold in other geographic markets). In this situation, information coded onto the test strip may be used by the test meter to determine that the test strip did not originate in the designated geographic market and therefore may not provide the features required by regulation, in which case the test may be aborted or flagged.

Further, a business model (subscription business model) may be applied for the distribution of test strips where proliferation of the test strips into other sales channels is not desired. For example, users may enroll into a subscription program in which they are provided with a test meter designed for use by subscription participants, and the subscription participants may be provided with subscription test strips on a regular basis (for example by mail or any other convenient form of delivery). Using the techniques of the present invention, the "subscription test strips" may be encoded to indicate that they were supplied to a subscription participant. For a variety of reasons, the manufacturer of the subscription test strips may not want the subscription test strips to be sold in other channels of trade. One way to prevent this is to design test meters provided to users who are not subscription participants that will not work with subscription test strips. Therefore, the present invention may be used to provide test meters to subscription participants in the subscription business model that are programmed to accept subscription test strips encoded to indicate that they are delivered to a user on the basis of a subscription, while other test meters are programmed not to accept subscription test strips so encoded.

As a further example, the test meter can have certain functionalities (software- and/or hardware-implemented) designed into the meter that are not active when the test meter is first sold. The performance of the test meter can then be upgraded at a later date by including information encoded on the test strips sold at that later time that will be recognized by the meter as an instruction to activate these latent features. As used herein, the phrase "activating a latent feature of the test meter" comprehends turning on a test meter functionality that previously was not active, such that the test meter functionality thereafter remains activated indefinitely (i.e. after the current test with the present test strip is finished).

Another example of information that can be encoded onto the test strip using the present invention is an indication of whether the test strip was sold to the hospital market or to the consumer market. Having this information may allow the test meter to take action accordingly, such as displaying user instructions in less detail for the hospital professional. It will be appreciated by those skilled in the art that a variety of types of communication between the test strip and the test meter may be facilitated by the information encoding provided by the present invention.

Systems and methods for encoding information onto a test strip are depicted in FIGS. 8-15. These encoding systems and methods are useful when used exclusively on a test strip, and can also be used in conjunction with other encoding systems and methods. Generally speaking, the encoding systems and methods depicted in FIGS. 8-15 provide for the resistance of at least one trace or trace loop, which is connected to a pair of associated contact pads, to be varied between test strips depending on the information to be encoded on each individual test strip. A test meter, in turn, measures the resistance of the trace or trace loop between a particular pair of contact pads on an inserted test strip, and decodes the resistance related information encoded on the test strip. In general, the test meter can determine in a digital sense which connections either exist or do not exist, and can measure in an analog sense the resistance between any connected contact pads. The ability for the test meter to obtain both digital and analog information allows the systems and methods of the present invention to be combined with other encoding systems. When combined with other encoding systems and methods, such as the encoding systems and methods disclosed in JP 2000/000352034 A2 and EP 1152239A1, which are hereby incorporated herein by reference in their entireties, the number of words that may be encoded on the test strip can be dramatically increased over that which can be encoded using the other system alone.

An alternate encoding scheme may also be used where the trace or trace loop resistance is ratioed, or proportionally compared, with at least one other trace or trace loop resistance. This alternate encoding scheme has benefits in compensating for inconsistencies that result from variations in trace or trace loop resistance from test strip to test strip.

In contrast to the encoding systems and methods of the present invention, some previous systems have examined test strip resistance as a fail-safe against inadvertent opens, scratches, or multiple point defects. Others have attempted to compensate for unwanted test strip trace resistance. Still other previous systems have merely determined whether a nontrivial trace resistance was present, and used the existence or nonexistence of the nontrivial resistance as a binary indicator of which of two types of strips was present—a strip intended for measurement or calibration purposes. In the systems that used resistance as a binary indicator, the determination of whether or not a particular trace had a nontrivial resistance was accomplished by comparing a measured resistance to a near-zero threshold resistance value. If the measured resistance was above the threshold value, the trace resistance was considered to be nontrivial, thereby indicating one type of strip. If the measured resistance was below the threshold value, the trace resistance was considered to be trivial and essentially zero, and the other type of strip was indicated. Thus, the system only distinguished between resistance values that were essentially zero and those that were not. Conversely, the systems and methods of the current invention are generally capable of distinguishing between at least two substantially non-zero resistance values.

In general, the systems and methods for encoding information on the test strip as disclosed in the present invention are useful to: discriminate between specific types of test strips; determine whether the inserted test strip matches a separate code key inserted into the test meter; encode calibration information directly onto the test strip; identify significant parameters related to the test strip such as country of origin, destination, or particular test strip chemistry; and determine which reagent is on the test strip. The systems and methods of the present invention are further useful in encoding information on a test strip that can be used for: choosing a language in which the test meter displays user operating instructions; determining if the test meter and test strip were sold in the same geographic market; preventing use of the test strip by the test meter if the test strip is a subscription test strip; activating a latent feature of the test meter; changing the user operating instructions; or performing other functions as would be obvious to one of ordinary skill in the art.

Figure 8:
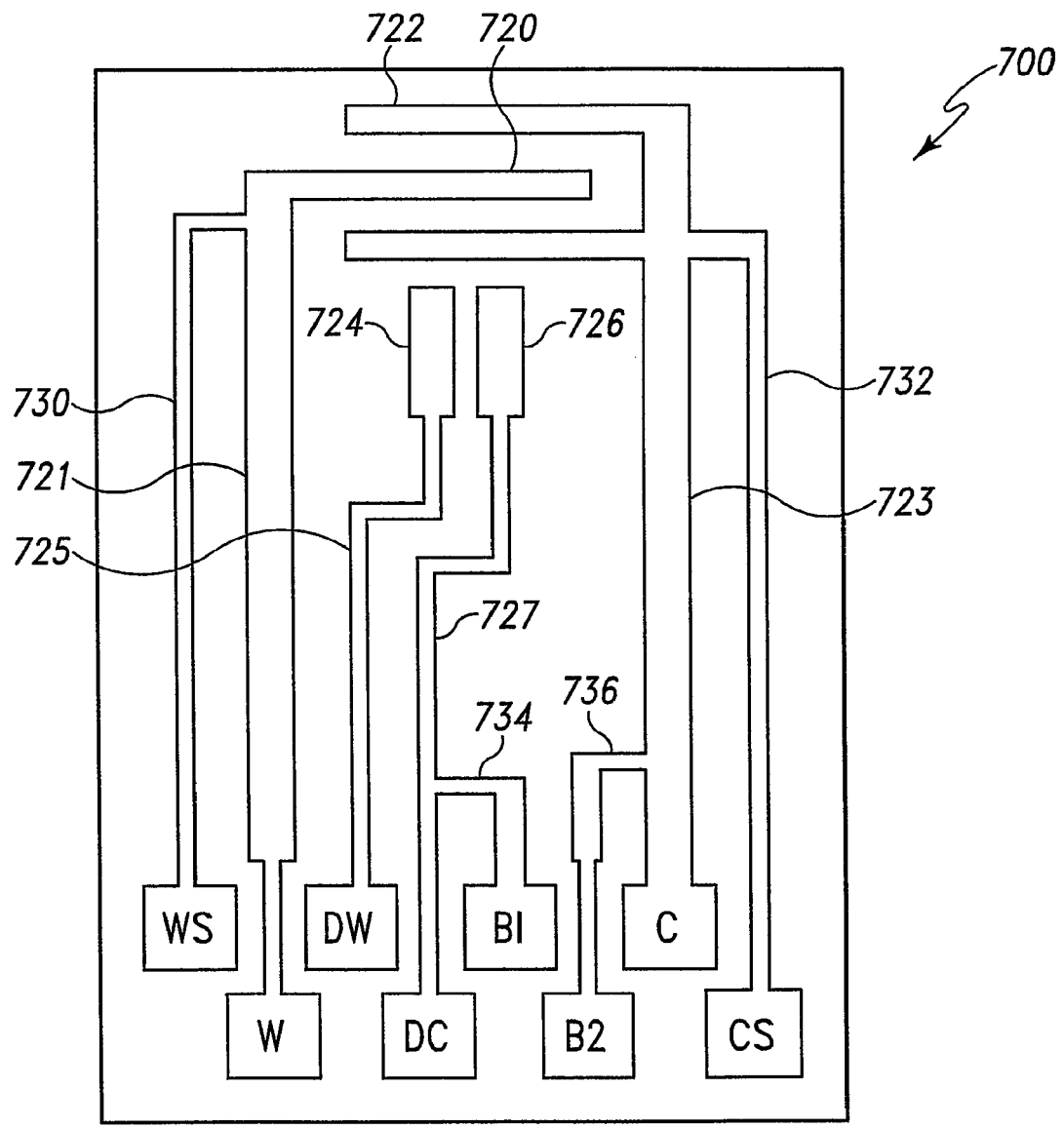
FIG. 8 is a schematic plan view of a second embodiment test strip electrode and contact pad arrangement according to the present invention.

A second embodiment test strip configuration that allows information to be encoded directly onto the test strip is illustrated in FIG. 8 and indicated generally at 700. The test strip 700 may be formed generally as described above with respect to the test strips 10 and 401, with working 720, counter 722, dose sufficiency working 724, and dose sufficiency counter 726 electrodes formed as shown and coupled, respectively, to working electrode 721, counter electrode 723, dose sufficiency working electrode 725, and dose sufficiency counter electrode 727 traces, which are further coupled, respectively, to measurement contact pads W, C, DW and DC. The test strip 700 further includes working electrode 730 and counter electrode 732 sense traces, which are coupled to measurement contact pads WS and CS, respectively. The contact pads provide a conductive area upon the test strip 700 to be contacted by an electrical connector contact for the test meter once the test strip 700 is inserted into the test meter. The electrical connector allows electrical signals to be applied from the test meter to the test strip and vice versa. The test strip may be formed with a sample inlet in the distal end of the test strip (as shown in FIG. 8), or with the sample inlet on the side of the test strip (as shown in FIG. 1), by way of example. The type of sample inlet is not related to the functionality of the embodiments described herein.

Referring to the traces connected to contact pads W and WS, the resistance along three portions between contact pads W and WS may be evaluated by a test meter: the resistance along working electrode trace 721 between contact pad W and the point where working electrode sense trace 730 connects, the resistance along sense trace 730 between contact pad WS and the point where electrode sense trace 720 connects, and the trace loop resistance between contact pads W and WS—"trace loop W-WS." In the first instance, a test meter can use working electrode sense trace 730 to measure the potential of working electrode trace 721 at the point where sense trace 730 connects to electrode trace 721 by using a voltage follower circuit or other similar method as known in the art (see, for example, the methods and circuits disclosed in co-pending application Ser. No. 10/961,352, which has been incorporated by reference hereinabove). Since the potential and current flow at contact pad W can be directly measured by the test meter, the change in potential, and thus the resistance, along working electrode trace 721 between contact pad W and the point where working electrode sense trace 730 intersects working electrode trace 721 can be calculated by the test meter. The resistance along working electrode sense trace 730 can be similarly calculated by the test meter.

Alternatively, the resistance of trace loop W-WS can be calculated by measuring the total change in potential between contact pads W and WS and the current flow therebetween. The calculated resistance along a trace loop includes the connector contact resistance between the test meter and the contact pads, the trace loop resistance, and the resistance of any analog switches in the test meter's measurement path. In an example embodiment, the trace loop W-WS is comprised of gold conductive material and has a nominal resistance of approximately 287 Ohms. In another example embodiment, the trace loop W-WS is comprised of palladium conductive material and has a nominal resistance of approximately 713 Ohms.

The resistance of a trace loop may be measured by AC or DC excitation. In one example embodiment, the W-WS loop resistance is measured by DC excitation while the C-CS loop resistance is measured by AC excitation. Other example embodiments utilize varying combinations of AC and/or DC excitation to measure trace and trace loop resistance on a test strip, some embodiments exclusively utilizing AC excitation with other embodiments exclusively utilizing DC excitation.

Referring to the traces connected to contact pads C and CS, the resistance along counter electrode trace 723 between contact pad C and the point where counter electrode sense trace 732 connects, the resistance along sense trace 732 between contact pad CS and the point where electrode trace 723 connects, and the trace loop C-CS resistance between contact pads C and CS can each be determined by a test meter in a manner similar to that described above with respect to the traces connected to contact pads W and WS. In an example embodiment, the trace loop C-CS is comprised of gold conductive material and has a resistance of approximately 285 Ohms. In another example embodiment, the trace loop C-CS is comprised of palladium conductive material and has a resistance of approximately 712 Ohms.

Test strip 700 also includes information traces 734 and 736, which are connected to information contact pads B1 and B2, respectively. Information traces 734 and 736 are further connected, respectively, to dose sufficiency counter electrode trace 727 and counter electrode trace 723. Not only can information contact pads B1 and B2 and their associated trace loops be used with the encoding systems and methods illustrated in FIGS. 1-15 and described above, the various trace resistance values of trace loops DC-B1 and C-B2 can be used to further encode information onto test strip 700. For example, the resistance values of trace 734, trace 736, the portion of trace 727 between contact pad DC and the point where trace 734 connects, the portion of trace 723 between contact pad C and the point where trace 736 connects, trace loop DC-B1, and trace loop C-B2 can all be individually measured and used to encode information on test strip 700 in a manner similar to that described above with respect to the traces connected to contact pads W and WS.

Information digitally encoded on a test strip provides a limited number of options to encode information, for example, the test strip may be limited to $2^N$ potential states or words, where N is the number of information contact pads on the test strip. In contrast, the resistance measured by a test meter is generally not limited to discrete values and any value along a continuum of potential trace resistance values may be measured. Thus, the number of words or states encodable on a test strip using a continuum of trace resistance values can exceed the number of words or states encodable on a test strip using discrete digital states, which generally only determine if a connection between two contact pads is present or not.

The number of potential words and the amount of information that can be encoded on a test strip using the resistance of test strip traces or trace loops is typically limited by the ability to precisely manufacture a particular trace resistance and the ability to accurately measure the same trace resistance. Given an ability to precisely control the resistance during manufacture and precisely measure a trace or trace loop resistance, a theoretically infinite amount of information can be encoded on a test strip, where each measurable resistance along the continuum corresponds to a different word or state. However, due to actual manufacturing and measurement capabilities, the number of available resistance values along the continuum is frequently restricted. To account for measurement and manufacturing errors, the number of available states along the continuum may be subdivided into a number of discrete ranges, where each discrete range corresponds to a different word or state, and the range of resistance values associated with each range is approximately as large as the cumulative measurement and manufacturing errors. In one example embodiment, the information as to the number of discrete ranges or size of each discrete range may be programmed onto a ROM key that is inserted into the test meter.

The method used to measure resistance and other factors, such as the temperature of the test strip and test meter, can also affect the resistance measured by the test meter and the minimum size of each discrete range that may be used. For example, in one embodiment of the present invention the measured trace or trace loop resistance includes the resistance of at least one analog switch internal to the test meter, where the analog switch resistance varies from 10 to 180 Ohms depending on the temperature and manufacturing tolerances. If, for illustrative purposes, it is assumed that the test meter has a resistance measurement accuracy of +/−30 Ohms, then the smallest size for each discrete range that may be used to encode information onto the test strip is at least 60 Ohms.

As stated above, one advantage of the trace or trace loop resistance encoding systems and methods is that they can be used in conjunction with other systems. Combining trace loop resistance encoding with other encoding methods can considerably increase the total number of words encodable on a test strip over that which can be encoded using the other methods alone, even when limiting the available states along the continuum of possible resistance values to discrete ranges.

As an example encoding system and method utilizing discrete ranges of resistances, it is assumed that the resistance along each of the W-WS and C-CS trace loops in FIG. 8 is limited to be within one of three measurable resistance ranges, represented by range numbers 1, 2, and 3. Thus, a total of nine different words can be encoded on test strip 700 by measuring the resistance of trace loops W-WS and C-CS: WS1/CS1, WS1/CS2, WS1/CS3, WS2/CS1, WS2/CS2, WS2/CS3, WS3/CS1, WS3/CS2, and WS3/CS3. Combining this resistance encoding scheme with another encoding scheme, the total number of states encodable can be increased by a factor of nine. For example, JP 2000/000352034 A2 potentially discloses a total of eight states encodable onto the side of a test strip with the measurement electrode. Combining the current example with JP 2000/000352034 A2 results in a total of 72 states that may be encoded onto a test strip. More generally, exclusively using the trace or trace loop resistance encoding systems and methods provides a total of $R^L$ unique words (R being the number of resistance states or ranges, and L being the number of trace loops) that may be encoded onto a test strip, while using the trace or trace loop resistance encoding system in conjunction with another encoding system provides an increase in the total words that may be encoded onto a test strip by a factor of $R^L$ over the other encoding system.

In general, the resistance in a particular trace as measured by a test meter varies, at least in part, with trace width, trace length, trace thickness, trace conductive material, trace temperature, and test meter switch resistance. Factors such as the exact width, length, thickness and conductive material of the trace can be controlled during manufacture, but manufacturing inconsistencies may result in unintentional variations in resistance resulting in trace resistance values different from what was intended. Furthermore, despite identical test strip mask configurations, these factors can further vary from test strip to test strip and production lot to production lot. However, the ratio of two trace or trace loop resistance values generally remains relatively consistent for a given test strip mask configuration despite these manufacturing inconsistencies. Thus, a technique that may be used by the test meter to counteract manufacturing inconsistencies is to ratio two trace or trace loop resistance measurement values. Using this or similar techniques, the test meter can effectively compensate for variations in resistance by evaluating resistance ratios between traces or trace loops, especially if necessary test meter analog switches are paired by type, size, process and package.

As an example, manufacturing inconsistencies in the amount of conductive material deposited on the substrate can result in trace thickness varying from test strip to test strip while trace width and length remain relatively constant for a given test strip mask configuration. However, these inconsistencies in the amount of conductive material deposited tend to vary slowly enough such that trace thickness tends to be uniform over a single test strip while varying from test strip to test strip. Thus, the ratio of trace resistance between two traces on the same test strip will remain essentially constant despite manufacturing inconsistencies.

Variations in trace width, length, thickness, and the material composition of the trace may be manipulated to control individual trace resistance values during manufacture since, as stated above, these characteristics affect the resistance of each trace. For example, the resistance of the C-CS trace loop can be reduced by either increasing the width of the counter electrode trace 723 or the counter electrode sense trace 732, or by decreasing the overall length of the loop. Similarly, the C-CS loop's resistance can be increased by decreasing the width of either trace 723 or 732, or by increasing the effective overall length of the loop.

Alternate embodiments utilize different test strip mask configurations. The number, location, or particular type of electrode traces to which the information traces may be connected can vary with the only limitation being that the functionality of the test strip can not be compromised by, for example, connecting any of the electrodes or electrode traces to one another.

Figure 9:
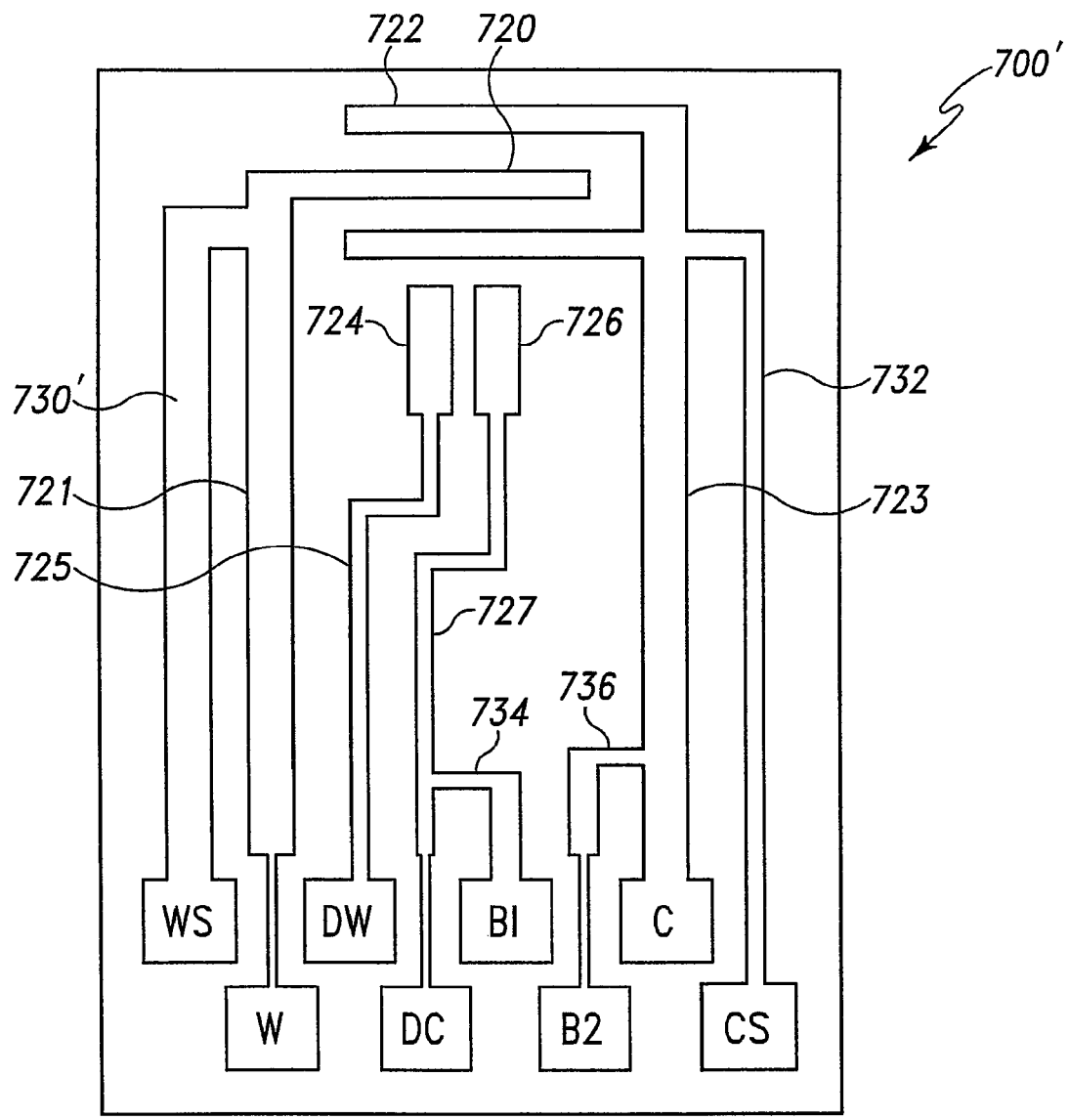
FIG. 9 is a schematic plan view the test strip electrode and contact pad arrangement of FIG. 8 illustrating a modified trace.

Referring now to FIG. 9, therein is depicted an alternate example embodiment test strip 700', which is similar to test strip 700 except as noted below. Working electrode sense trace 730' is wider than working electrode sense trace 730. In this example alternate embodiment, the W-WS trace loop resistance in test strip 700' is less than the W-WS trace loop resistance in test strip 700. Similarly, the ratio of the W-WS loop resistance to C-CS loop resistance in test strip 700' is less than the ratio of the W-WS loop resistance to C-CS loop resistance in test strip 700 due to the increased width in sense trace 730'. Thus, information is encoded on test strips 700 and 700' by varying trace width. A test meter may therefore distinguish between test strip 700 and test strip 700' by, for example, measuring the absolute resistance in trace loop W-WS, measuring the absolute resistance in a segment of trace loop W-WS, or by determining the ratio of the W-WS trace loop resistance and the C-CS trace loop resistance.

Figure 10:
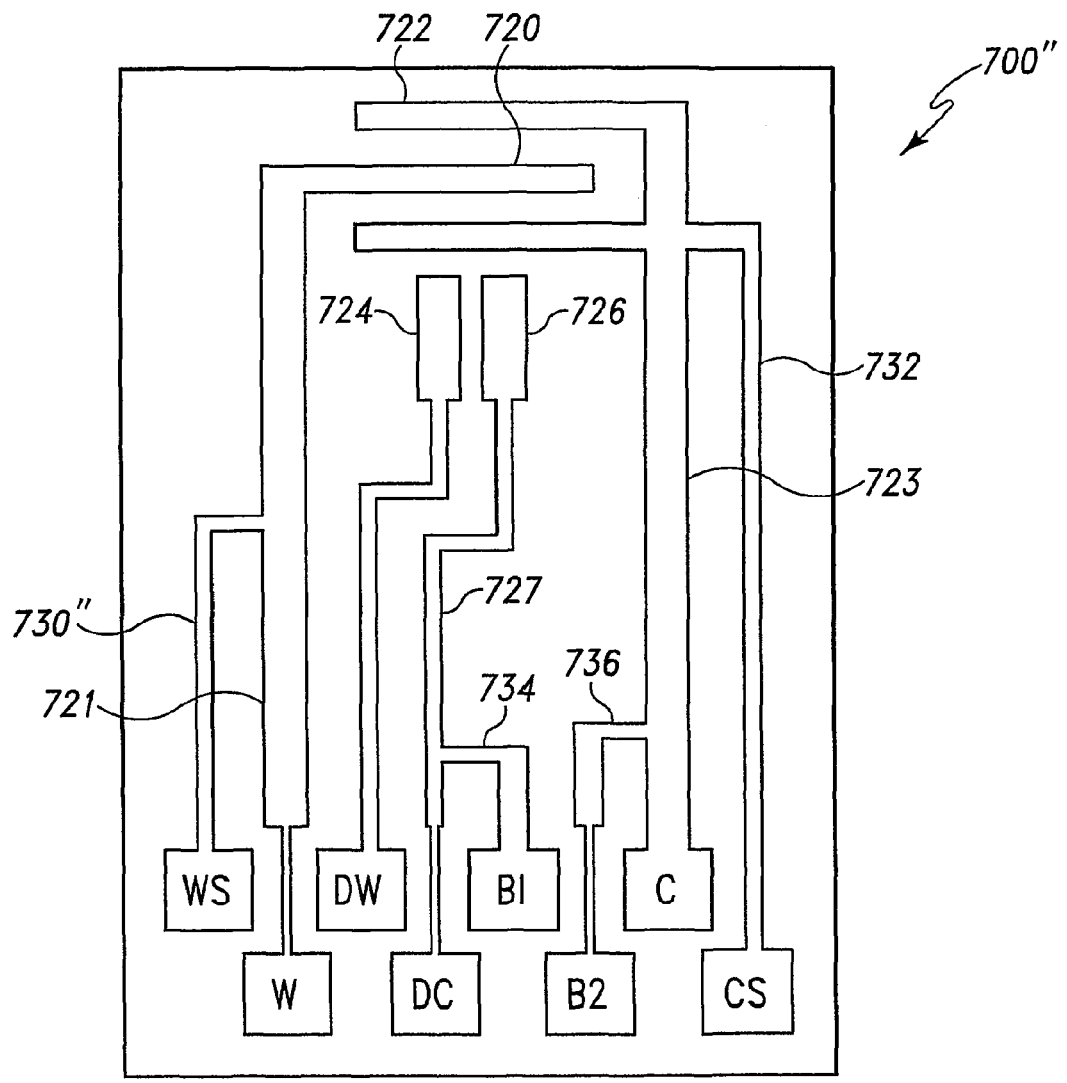
FIG. 10 is a schematic plan view the test strip electrode and contact pad arrangement of FIG. 8 illustrating another modified trace.

Referring now to FIG. 10, therein is depicted yet another example embodiment test strip 700", which is similar to test strip 700 except as noted below. Test strip 700" includes alternate working electrode sense trace 730". Sense trace 730" differs from sense trace 730 in that sense trace 730" is shorter than sense trace 730. In this example alternate embodiment, the W-WS trace loop resistance in test strip 700" is less than the W-WS trace loop resistance in test strip 700. Similarly, the ratio of the W-WS loop resistance to C-CS loop resistance in test strip 700" is less than the ratio of the W-WS loop resistance to C-CS loop resistance in test strip 700 due to the decreased length in sense trace 730". Thus, information is encoded on test strips 700 and 700' by varying trace length. A test meter may therefore distinguish between test strip 700 and test strip 700" by, for example, measuring the absolute resistance in trace loop W-WS, measuring the absolute resistance in a segment of trace loop W-WS, or by determining the ratio of the W-WS trace loop resistance and the C-CS trace loop resistance.

Figure 11:
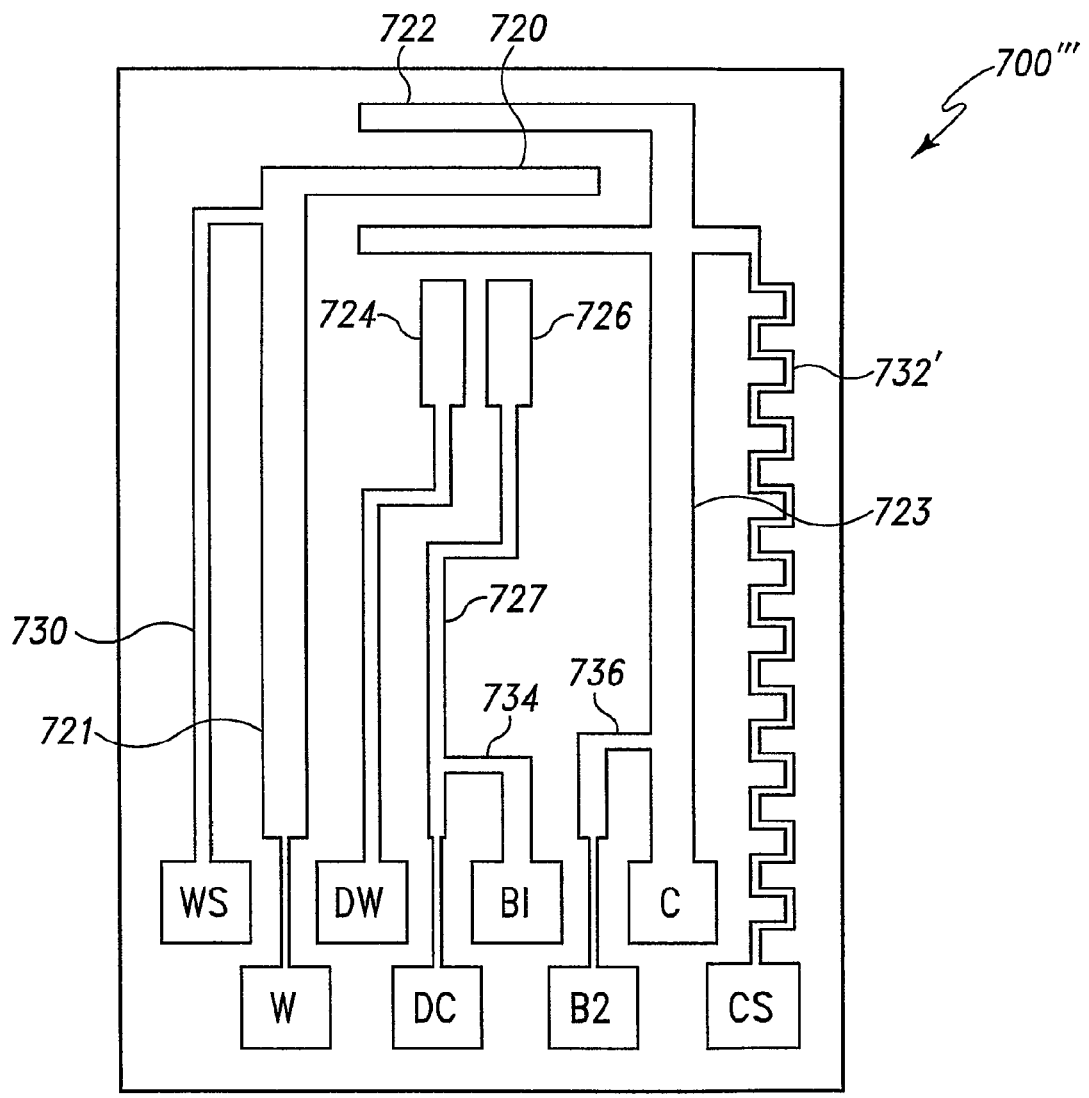
FIG. 11 is a schematic plan view the test strip electrode and contact pad arrangement of FIG. 8 illustrating yet another modified trace.

FIG. 11 depicts still another example embodiment test strip 700''', which is a variation of test strip 700 and differs from test strip 700 as noted below. Test strip 700''' includes counter electrode sense trace 732', which has a longer and narrower electrical path length and, consequently, a higher resistance than sense trace 732. In this example alternate embodiment, the C-CS trace loop resistance in test strip 700''' is greater than the C-CS trace loop resistance in test strip 700. Similarly, the ratio of the W-WS loop resistance to C-CS loop resistance in test strip 700''' is less than the ratio of the W-WS loop resistance to C-CS loop resistance in test strip 700 due to the increased length in sense trace 732'. Thus, information is encoded on test strips 700 and 700' by varying trace length. A test meter may therefore distinguish between test strip 700 and test strip 700''' by, for example, measuring the absolute resistance in trace loop C-CS, measuring the absolute resistance in a segment of trace loop C-CS, or by determining the ratio of the W-WS trace loop resistance and the C-CS trace loop resistance.

Figure 12:
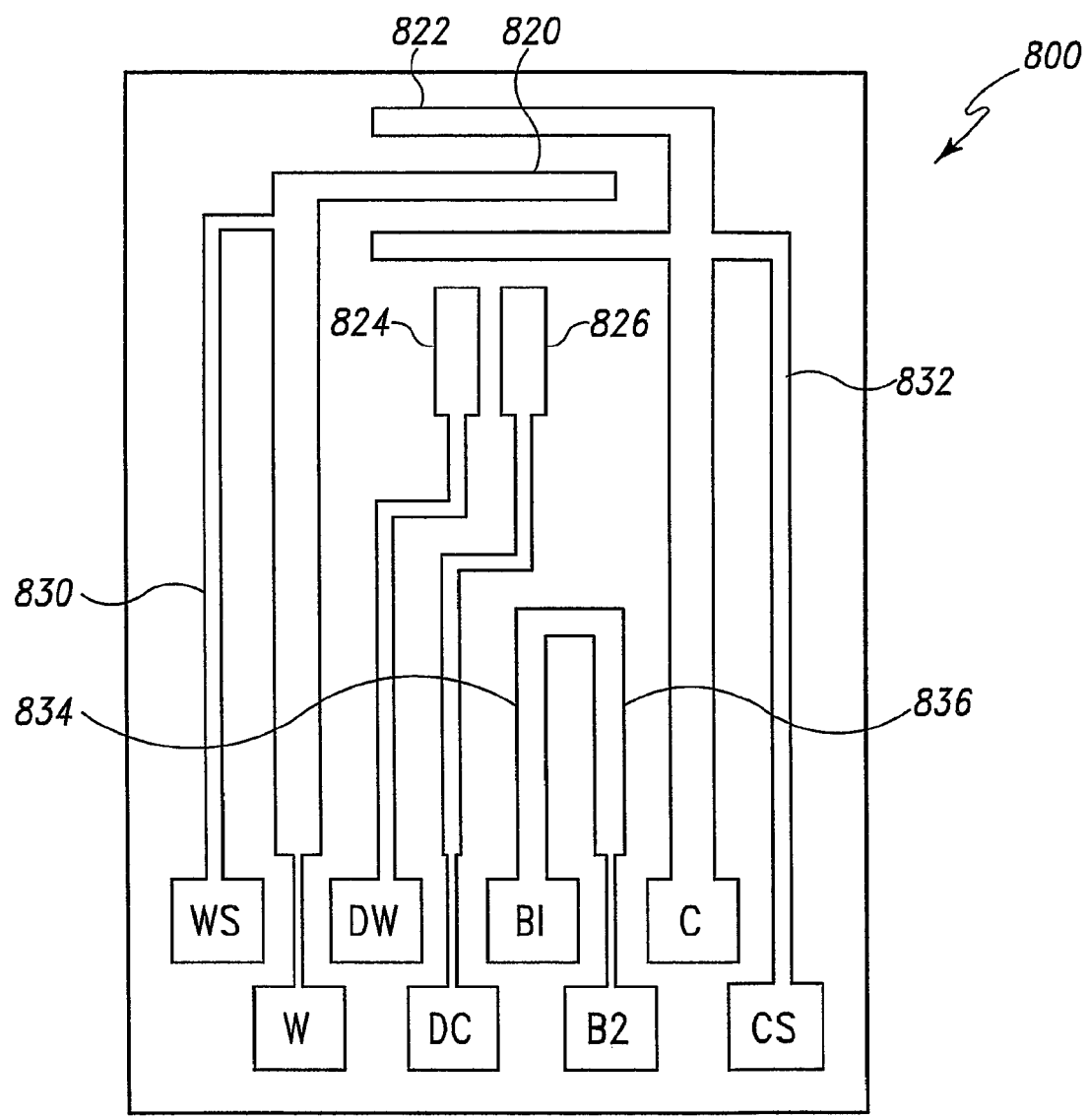
FIG. 12 is a schematic plan view of a third embodiment test strip electrode and contact pad arrangement according to the present invention.

A third embodiment test strip configuration is illustrated in FIG. 12 and indicated generally at 800. The test strip 800 is generally similar to test strip 700 described above except as otherwise indicated, with working electrode 820, counter electrode 822, dose sufficiency working electrode 824, dose sufficiency counter electrode 826, working electrode sense trace 830, and counter electrode sense trace 832 formed as shown and coupled, respectively, to measurement contact pads W, C, DW, DC, WS and CS. In contrast to test strip 700, test strip 800 includes information trace 834 and information trace 836, which are connected to information contact pads B1 and B2, respectively, and further connected to each other. These contact pads provide a conductive area upon the test strip 800 to be contacted by an electrical connector contact of the test meter once the test strip 800 is inserted into the test meter.

In the depicted embodiment of the test strip 800, information trace 834 and information trace 836 combine to provide a trace loop B1-B2 between information contact pads B1 and B2. Resistance of at least one information trace 834 and 836 can be varied to encode information in addition to that which may be encoded using trace loops W-WS and C-CS. When inserted into a test meter, test strip 800 is distinguishable from test strip 700 since contact pads DC and B1 are not connected, since contact pads C and B2 are not connected, and since contact pads B1 and B2 are connected. Test strip 800 is further distinguishable from test strip 700 based on the measured value of the B1-B2 loop resistance. Generally speaking, the test meter can determine in a digital sense which connections either exist or do not exist, and can measure in an analog sense the resistance between any connected contact pads. The resistance of information traces 834 and 836 can be varied during manufacture by varying the width, thickness, length, or material utilized to construct information traces 834 and 836.

Figure 13:
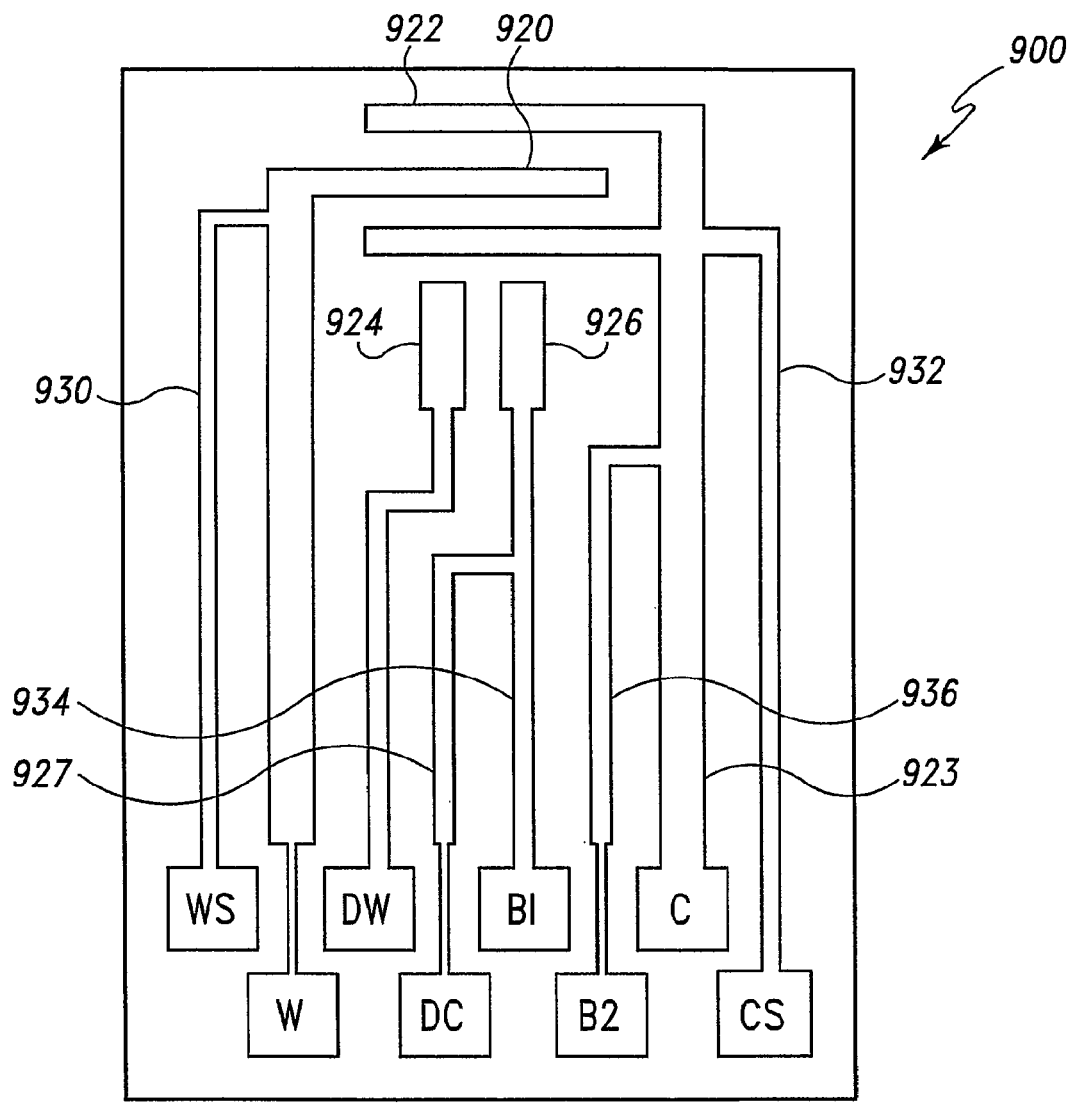
FIG. 13 is a schematic plan view of a fourth embodiment test strip electrode and contact pad arrangement according to the present invention.

A fourth embodiment test strip configuration is illustrated in FIG. 13 and indicated generally at 900. The test strip 900 may be formed with working electrode 920, dose sufficiency working electrode 924, information trace 934 and information trace 936 being formed as shown and coupled, respectively, to measurement contact pads W and DW, and to information contact pads B1 and B2. Additionally, the test strip 900 includes counter electrode 922 and dose sufficiency counter electrode 926 connected, respectively to counter electrode trace 923 and dose sufficiency counter electrode trace 927, which in turn are further connected to measurement contact pads C and DC, respectively. Similar to the test strips 700 and 800, the contact pads provide a conductive area upon the test strip 900 to be contacted by an electrical connector contact of the test meter once the test strip 900 is inserted into the test meter.

In the example embodiment test strip 900, information trace 934 is electrically connected to dose sufficiency counter electrode trace 927, and information trace 936 is electrically connected to counter electrode trace 923. These electrical connections provide additional trace loops where the resistance may be measured between contact pads DC and B1, and C and B2. When connected to a test meter, the lack of electrical connection between contact pads B1 and B2, the presence of an electrical connection between contact pads B1 and DC, and the presence of an electrical connection between B2 and C each separately be used to encode information and distinguish test strip 900 from test strip 800. Additionally, the resistance along dose sufficiency counter electrode trace 927, information trace 934, information trace 936, and counter electrode trace 923 can further encode additional information concerning test strip 900.

Furthermore, when compared with test strip 700, information traces 934 and 936 are longer and have more resistance than information traces 734 and 736. Thus, the DC-B1 and C-B2 trace loop resistances in test strip 900 are, respectively, greater than the DC-B1 and C-B2 trace loop resistances in test strip 700. Thus, a test meter may distinguish between test strip 900 and test strip 700 by, for example, measuring the absolute resistance in trace loops DC-B1 or C-B2, or by comparing the resistance ratios of either trace loops DC-B1 or C-B2 to one another or to other trace loops, such as trace loops W-WS or C-CS.

Figure 14:
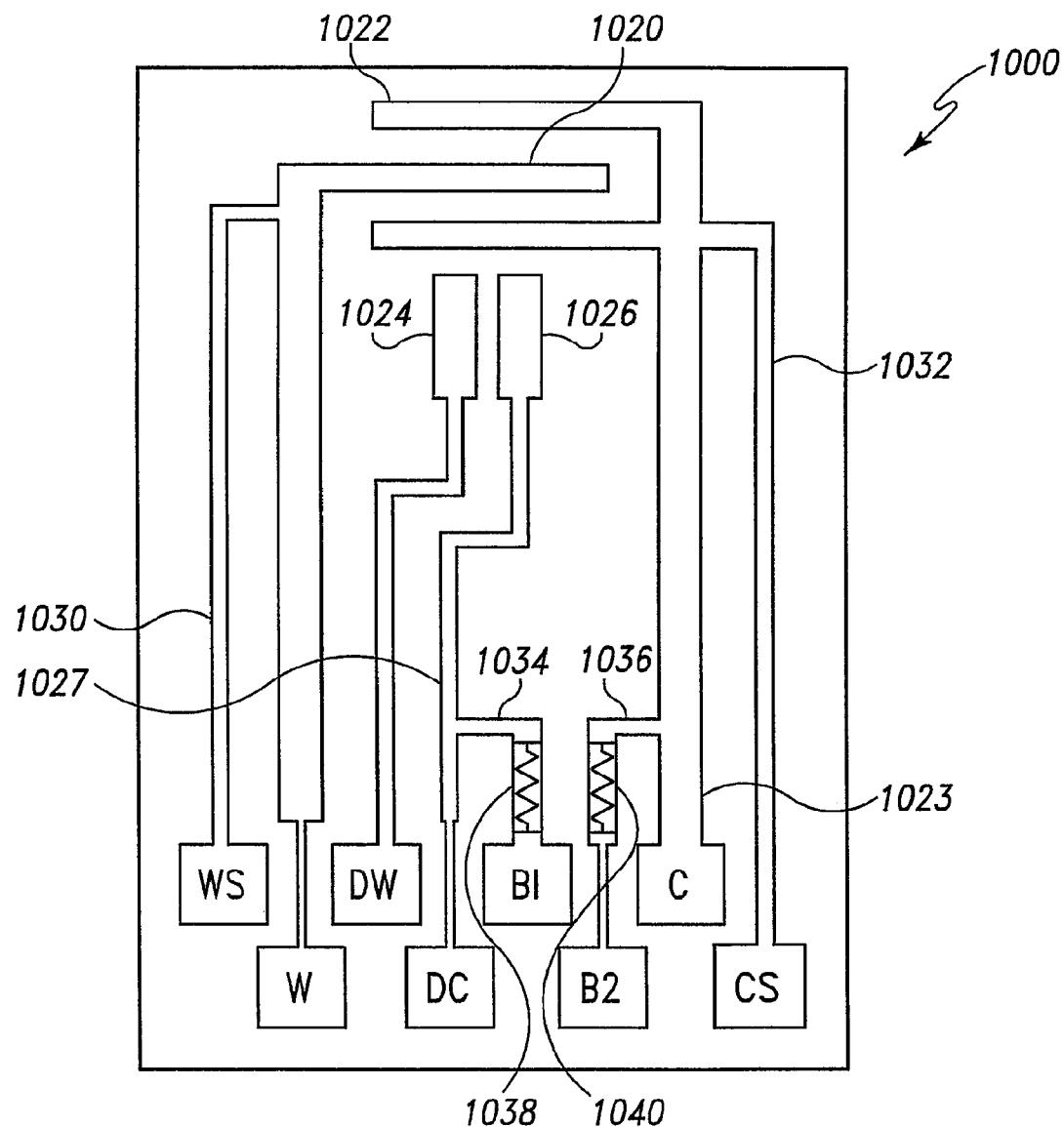
FIG. 14 is a schematic plan view of a fifth embodiment test strip electrode and contact pad arrangement according to the present invention.
Figure 15:
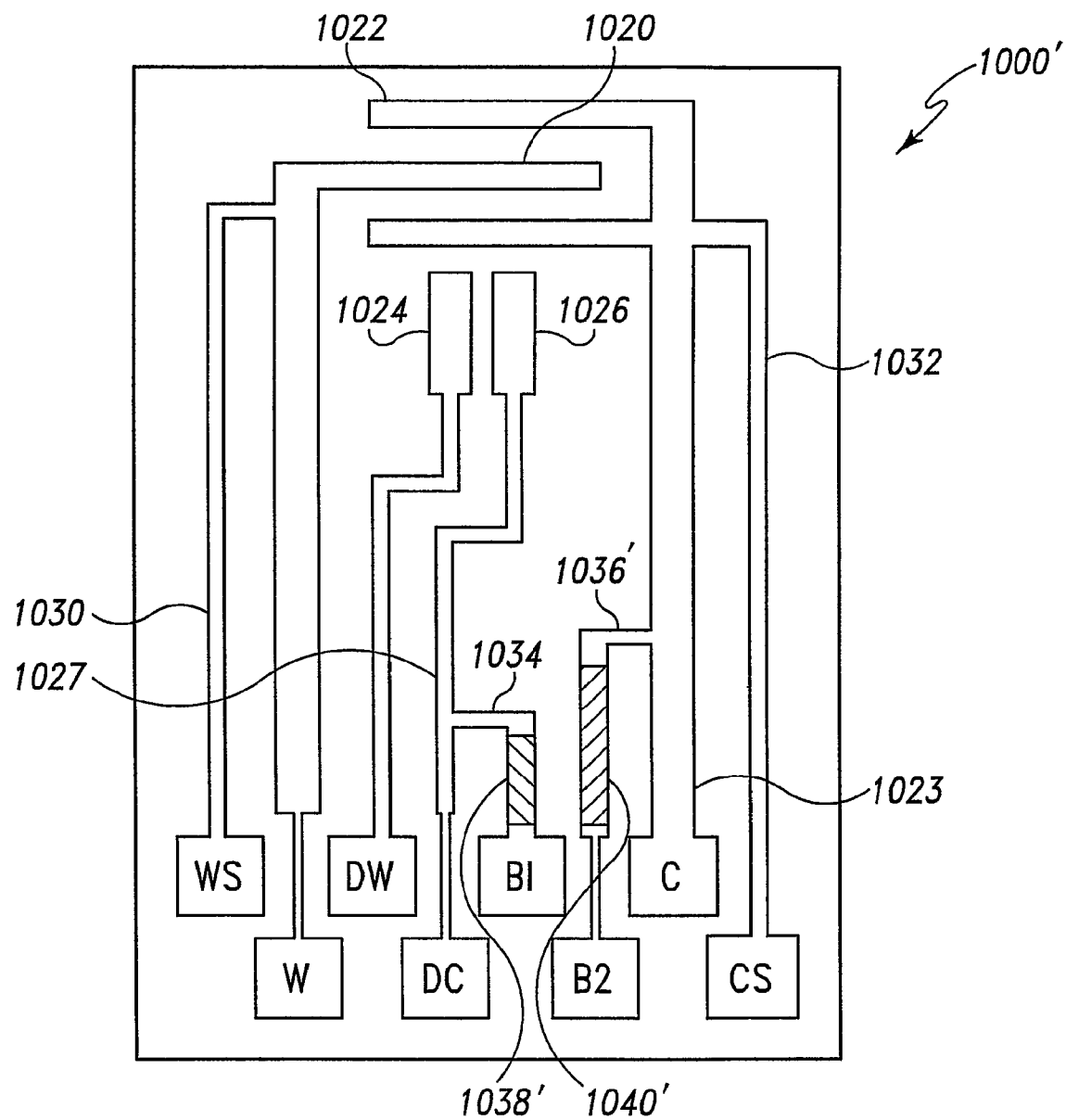
FIG. 15 is a schematic plan view the test strip electrode and contact pad arrangement of FIG. 14 illustrating alternate resistive elements and a modified trace.

Turning now to FIGS. 14 and 15, therein is depicted an fifth embodiment test strip 1000 that allows information to be encoded directly on the test strip. The test strip 1000 may be formed with working electrode 1020, dose sufficiency working electrode 1024, working electrode sense trace 1030, counter electrode sense trace 1032, information trace 1034, and information trace 1036 formed as shown and coupled, respectively, to measurement contact pads W, DW, WS and CS, and information contact pads B1 and B2. Additionally, counter electrode 1022 and dose sufficiency counter electrode 1026 are connected, respectively, to counter electrode trace 1023 and dose sufficiency counter electrode trace 1027, which are in turn further connected, respectively, to measurement contact pads C and DC. Information trace 1034 includes resistive element 1038 and is connected to dose sufficiency counter electrode trace 1027. Information trace 1036 includes resistive element 1040 and is connected to counter electrode trace 1023. The contact pads provide a conductive area upon the test strip 1000 to be contacted by an electrical connector contact of the test meter once the test strip 1000 is inserted into the test meter.

As depicted in FIGS. 14 and 15, trace loops DC-B1 and C-B2 are formed between measurement pads DC and B1, and C and B2, respectively. As described above, the resistance of trace loops DC-B1 and C-B2 can be controlled during manufacture by varying the width, thickness, length, or material of the trace loops. However, having a large number of different test strip mask configurations in order to provide a large number of encoded words or states can be difficult and expensive during manufacture. One method by which the total number of test strip mask configurations may be reduced is to use a single mask configuration with a location along a trace where a resistive element can be included and integrated into the trace. This method can be extended to integrating multiple resistive elements into one or more traces. During manufacture, the resistance of a particular trace can be controlled by varying the resistance of the resistive element, or elements, included in a particular trace, thus providing a simple and convenient manner to control trace or trace loop resistance.

As an illustrative example, test strip 1000 in FIG. 14 utilizes a film-type resistive element 1038 in information trace 1034. Thus, the overall resistance in both information trace 1034 and trace loop B1-DC includes the resistance of resistive element 1038. Similarly, the overall resistance in both information trace 1036 and trace loop C-B2 includes the resistance of resistive element 1040. During manufacture, the test strip 1000 may be initially formed using a test strip mask configuration with gaps in information traces 1034 and 1036. Later, resistive elements 1038 and 1034 are placed to span the gaps in information traces 1034 and 1036, respectively.

Now referring to FIG. 15, the test strip 1000' depicts an embodiment where the DC-B1 trace loop resistance in FIG. 15 differs from the DC-B1 trace loop resistance in FIG. 14, while the C-B2 trace loop resistance in FIG. 15 is equivalent to the C-B2 trace loop resistance in FIG. 14. The test strip 1000' utilizes a relatively similar basic overall mask configuration as the test strip 1000 with gaps initially formed in information traces 1034 and 1036' and with information trace 1036' being longer than information trace 1036. In contrast to the test strip 1000, the gaps in test strip 1000' are spanned by a conductive ink to form resistive elements 1038' and 1040'. The conductive ink will be assumed for this example to have less resistance for a given length than the film-type resistive elements used in FIG. 14. The resistance of resistive element 1038' is less than the resistance of resistive element 1038, thus, the resistance of trace 1034 in FIG. 15 is less than the resistance of trace 1034 in FIG. 14. However, the increased length of trace loop C-B2 and the increased length of resistive element 1040' result in the resistance of trace loop C-B2 in FIG. 15 equaling the resistance in trace loop C-B2 in FIG. 14. Thus, a test meter can distinguish between test strip 1000 and test strip 1000' by measuring, for example, the resistance in trace 1034, the resistance in trace loop DC-B1 in, or the ratio of trace loop DC-B1 resistance and trace loop C-B2 resistance.

Resistive elements 1038, 1038', 1040 and 1040' may be comprised of different conductivity materials as are commonly known in the art for modifying trace resistance. These materials include conductive ink, screen printing thick film hybrid resistors, and standard fixed value thick or thin film resistors.

In general, the total number of possible states that may be encoded on a test strip using the system and methods illustrated herein and described above is limited by the space available on the test strip surface or materials available for manipulating trace or trace loop resistance; the ability to accurately control the resolution of the conductive features on the test strip, such as trace or trace loop size, shape, and placement; and the ability to accurately measure the resistance values on the test strip. An enhanced ability to accurately control trace geometry decreases the manufacturing related variation in trace resistance and allows additional words or states to be encoded on a test strip for a given test strip size and shape. Similarly, an enhanced ability to accurately control trace geometry allows for an increased number of traces and information contact pads to be placed on a test strip, thereby allowing additional words or states to be encoded on a test strip for a given test strip size and shape.

It should be noted that the ability to precisely control trace geometry and increase the trace and contact pad densities as achieved in the present invention through the use of the laser ablation process represent a significant advancement over the prior art. The laser ablation process described hereinabove allows for resolution of test strip conductive features not previously achievable using prior art techniques such as screen printing and photolithography. Because of this, relatively large quantities of data can be coded onto the test strip when the conductive features are formed using the laser ablation process. For example, published European patent application EP 1 024 358 A1 discloses a system which uses up to 35 contact pads on a single test strip; however, the density of features is so low that the inventors are forced to contact only five of those contact pads at any one time. Not only does this require much more test strip surface area than the present invention to form the same number of contact pads, but it is impossible for the test meter to measure the resistance between each of the contact pads because the test meter is never in contact with more than five of the contact pads at any one time. The tight control of feature dimensions enabled by the laser ablation process of the present invention allows for the use of trace and contact pad densities never before achieved in the art.

It should also be appreciated that the term trace loop is not intended to be limiting and does not imply a particular trace geometry, such as a circular path, and includes any portion of an electrical pathway along which resistance can be determined.

It should be further appreciated that test strip characteristics by which a test meter can distinguish between two or more test strips are characteristics that can be utilized to encode information on a test strip.

All publications, prior applications, and other documents cited herein are hereby incorporated by reference in their entirety as if each had been individually incorporated by reference and fully set forth.

While the invention has been illustrated and described in detail in the drawings and foregoing description, the description is to be considered as illustrative and not restrictive in character. Only the illustrated embodiments, and certain other embodiments deemed helpful in further explaining how to make or use the illustrated embodiments, have been shown. All changes and modifications that come within the spirit of the invention are desired to be protected.

What is claimed is:

1. An electrochemical test strip for measuring a concentration of an analyte of interest in a biological fluid, the test strip comprising:
    a substrate;
    a plurality of data encoded on the test strip;
    a measurement electrode formed on the substrate;
    a first trace loop formed on the substrate, the first trace loop having a first associated resistance;
    a second trace loop formed on the substrate, the second trace loop having a second associated resistance, wherein the first and second resistances define a first resistance ratio corresponding to at least one of the plurality of data encoded on the test strip; and
    at least a third trace loop formed on the substrate, the identity of which of the plurality of encoded data corresponds to the first resistance ratio being indicated by at least one of the following:
        a. connection or lack of connection between the third trace loop and another trace loop,
        b. the resistance associated with the third trace loop, and
        c. the ratio of the resistance of the third trace loop with the resistance of another trace loop.

2. The electrochemical test strip of claim 1 in which the third trace loop is connected to only the first trace loop, the connection between the third trace loop and the first trace loop, and the lack of connection between the third trace loop and the second trace loop, indicating which of the plurality of data corresponds to the first resistance ratio.

3. The electrochemical test strip of claim 1 in which the third trace loop is connected to both the first trace loop and the second trace loop, the connection between the third trace loop with both the first and second trace loops indicating which of the plurality of data corresponds to the first resistance ratio.

4. The electrochemical test strip of claim 1 in which the third trace loop is connected to only the first trace loop, said test strip further comprising:
    a fourth trace loop formed on the substrate and connected to only the first trace loop, only the second trace loop, or both the first and second trace loops, the connection between the third trace loop and the first trace loop, together with the connection between the fourth trace loop and one or more other trace loops, indicating which of the plurality of data encoded on the test strip corresponds to the first resistance ratio.

5. The electrochemical test strip of claim 4 in which the fourth trace loop is connected to the first trace loop.

6. The electrochemical test strip of claim 4 in which the fourth trace loop is connected to the second trace loop.

7. The electrochemical test strip of claim 4 in which the fourth trace loop is only connected to the second trace loop.

8. The electrochemical test strip of claim 1 and further comprising:
    a fourth trace loop formed on the substrate, the connection or lack of connection between the third trace loop and the fourth trace loop indicating which of the plurality of data corresponds to the first resistance ratio.

9. The electrochemical test strip of claim 8 in which the fourth trace loop is connected to the third trace loop.

10. The electrochemical test strip of claim 1 in which the third trace loop has a third associated resistance, the third resistance indicating which of the plurality of data corresponds to the first resistance ratio.

11. The electrochemical test strip of claim 1 in which the third trace loop has a third associated resistance, the first and third resistances defining a second resistance ratio indicating which of the plurality of data corresponds to the first resistance ratio.

12. The electrochemical test strip of claim 1 in which the third trace loop has a third associated resistance, said test strip further comprising:
    a fourth trace loop formed on the substrate and having a fourth associated resistance, the third and fourth resistances defining a second resistance ratio indicating which of the plurality of data corresponds to the first resistance ratio.

13. The electrochemical test strip of claim 1, wherein the plurality of data includes data indicative of one or more of the following:
    what analyte the respective test strip is designed to measure,
    what biological fluid the respective test strip is designed to receive,
    what calibration data is to be used with the respective test strip,
    what production lot the respective test strip was manufactured in,
    a calibration family of the respective test strip,
    a reagent disposed on the respective test strip,
    a geographic market in which the respective test strip is to be sold,
    a geographic market in which the respective test strip was manufactured,
    a display language to be used by a test meter into which the respective test strip is to be inserted,
    user operating instructions to be displayed by a test meter into which the respective test strip is to be inserted,
    that the respective test strip is to be sold on a subscription basis,
    that the respective test strip is not to be sold on a subscription basis,
    a latent feature to be activated by a test meter when the respective test strip is inserted into the test meter,
    that the respective test strip is to be sold in a hospital market, and
    that the respective test strip is to be sold in a consumer market.

14. The electrochemical test strip of claim 1, wherein the trace loops are selected from the group consisting of: conductive ink, screen printed thick film hybrid resistor, fixed value thick film resistor, and fixed value thin film resistor.

15. The electrochemical test strip of claim 1, wherein the resistances of the trace loops are determined by one or more items selected from the group consisting of:
- the dimensions of the respective trace loop,
- the material from which the respective trace loop is made, and
- at least one resistive element bridging a gap in the trace loop.

* * * * *